United States Patent
Shukla et al.

(10) Patent No.: US 11,270,797 B1
(45) Date of Patent: Mar. 8, 2022

(54) MACHINE-LEARNING BASED QUERY CONSTRUCTION AND PATTERN IDENTIFICATION FOR HEREDITARY ANGIOEDEMA

(71) Applicant: HVH Precision Analytics LLC, King of Prussia, PA (US)

(72) Inventors: Oodaye Shukla, Chesterbrook, PA (US); Donna Yosmanovich, King of Prussia, PA (US); Manjula Kasoji, King of Prussia, PA (US); Amy Finkbiner, King of Prussia, PA (US); Robert Lauer, Phoenixville, PA (US); Rauf Izmailov, King of Prussia, PA (US)

(73) Assignee: HVH Precision Analytics LLC, King of Prussia, PA (US)

( * ) Notice: Subject to any disclaimer, the term of this patent is extended or adjusted under 35 U.S.C. 154(b) by 639 days.

(21) Appl. No.: 15/724,480

(22) Filed: Oct. 4, 2017

Related U.S. Application Data

(60) Provisional application No. 62/404,338, filed on Oct. 5, 2016.

(51) Int. Cl.
*G16H 50/20* (2018.01)
*G06N 5/04* (2006.01)
(Continued)

(52) U.S. Cl.
CPC .......... *G16H 50/20* (2018.01); *G06F 16/242* (2019.01); *G06F 16/27* (2019.01); *G06N 5/047* (2013.01); *G06N 7/005* (2013.01); *G06N 20/00* (2019.01)

(58) Field of Classification Search
None
See application file for complete search history.

(56) References Cited

U.S. PATENT DOCUMENTS 8,068,993 B2 11/2011 Karlov et al.
2009/0171871 A1 7/2009 Zhang et al.
(Continued)

FOREIGN PATENT DOCUMENTS

WO WO2016094330 6/2016
WO WO2018090009 5/2018
(Continued)

OTHER PUBLICATIONS

Kvancz, Predictive Analytics: A Case Study in Machine-Learning and Claims Databases, Dec. 2016 (Year: 2016).*
(Continued)

*Primary Examiner* — Robert W Morgan
*Assistant Examiner* — Andrew E. Lee
(74) *Attorney, Agent, or Firm* — Heslin Rothenberg Farley & Mesiti; Kristian E. Ziegler, Esq.; Rachel L. Pearlman, Esq.

(57) ABSTRACT

A method, computer program product, and system identifying a probability of a medical condition in a patient. The method includes a processor obtaining data set(s) related to a patient population diagnosed with a medical condition and based on a frequency of features in the data set(s), identifying common features and weighting the common features based on frequency of occurrence in the data set(s) to generate mutual information. The processor generates pattern(s) including a portion of the common features to generate a machine learning algorithm(s). The processor compiles a training set of data to use to tune the machine learning algorithm(s). The processor dynamically adjusts common features in the pattern(s) such that the machine learning algorithm(s) can distinguish patient data indicating the medical condition from patient data not indicating the medical condition. The processor applies the machine learn- (Continued)

ing algorithm(s) to data related to the undiagnosed patient, to determine the probability.

18 Claims, 12 Drawing Sheets

(51) Int. Cl.
*G06N 7/00* (2006.01)
*G06N 20/00* (2019.01)
*G06F 16/27* (2019.01)
*G06F 16/242* (2019.01)

(56) References Cited

U.S. PATENT DOCUMENTS

| | | | | |
|---|---|---|---|---|
| 2009/0171956 | A1* | 7/2009 | Gupta | G06F 16/35 |
| 2012/0271612 | A1* | 10/2012 | Barsoum | G06F 19/00 |
| | | | | 703/11 |
| 2013/0071860 | A1* | 3/2013 | Hale | G01N 33/564 |
| | | | | 435/7.24 |
| 2013/0238533 | A1* | 9/2013 | Virkar | G06N 20/10 |
| | | | | 706/12 |
| 2013/0262357 | A1 | 10/2013 | Amarasingham et al. | |
| 2014/0095201 | A1* | 4/2014 | Farooq | G16H 50/30 |
| | | | | 705/3 |
| 2014/0278448 | A1* | 9/2014 | Sadeghi | G16H 15/00 |
| | | | | 705/2 |
| 2014/0279746 | A1* | 9/2014 | De Bruin | G16H 20/70 |
| | | | | 706/12 |
| 2015/0324527 | A1 | 11/2015 | Siegel et al. | |
| 2016/0063212 | A1* | 3/2016 | Monier | G16H 50/50 |
| | | | | 705/3 |
| 2017/0053665 | A1 | 2/2017 | Quatieri, Jr. et al. | |
| 2017/0124269 | A1* | 5/2017 | McNair | G16H 10/60 |
| 2017/0198349 | A1 | 7/2017 | Rice | |
| 2017/0262604 | A1* | 9/2017 | Francois | G16H 50/20 |
| 2017/0286622 | A1* | 10/2017 | Cox | G06F 19/00 |
| 2017/0308981 | A1 | 10/2017 | Razavian et al. | |
| 2019/0019581 | A1 | 1/2019 | Vaughan et al. | |
| 2019/0138693 | A1* | 5/2019 | Muller | G16H 50/20 |
| 2020/0151627 | A1 | 5/2020 | Shukla et al. | |

FOREIGN PATENT DOCUMENTS

| | | |
|---|---|---|
| WO | WO2020102220 | 5/2020 |
| WO | WO2020132468 | 6/2020 |

OTHER PUBLICATIONS

Speiser et al., "Random Forest Classification of Etiologies for an Orphan Disease", Statistics in Medicine, 34, 887-899, doi: 10.1002/sim6351, Year: 2015.

Huw Llewelyn, "Reasoning in Medicine and Science", Sep. 2015, https:/blog.oup.com/2013/09/medical-diagnosis-reasoning-probable-eliminationn/ (Acessed via Wayback machine).

International Search Report and Written Opinion of International Application No. PCT/US2019/060962, dated Mar. 9, 2020, 9 pages.

International Search Report and Written Opinion for International Application No. PCT/US2019/067893, dated Mar. 15, 2020, 8 pages.

* cited by examiner

MACHINE-LEARNING BASED QUERY CONSTRUCTION AND PATTERN IDENTIFICATION FOR HEREDITARY ANGIOEDEMA

CROSS-REFERENCE TO RELATED APPLICATIONS

This application claims priority to U.S. Provisional Application No. 62/404,338 filed Oct. 5, 2016, entitled, "MACHINE-LEARNING BASED QUERY CONSTRUCTION AND PATTERN IDENTIFICATION" which is incorporated herein by reference in its entirety.

FIELD OF INVENTION

The invention relates to the creation and utilization of machine-based learning algorithms to establish and identify data patterns in the absence of established knowledge regarding these patterns.

BACKGROUND OF INVENTION

Health patterns indicative of certain health conditions are often difficult to identify. This is true for diseases and medical conditions that are readily known to the general population, as well as with diseases that are so rare that they affect only a small portion of the population.

Some diseases, although known to the general public, are clinically diagnosed through exclusion. Thus, a diagnosis of the disease can be delayed as each other possibility is systematically excluded. This prolonged diagnostic time can be detrimental as it delays initiating approved treatments and the progression of the disease for an undiagnosed patient may preclude that patient, when finally diagnosed, from enrolling in a clinical trial and/or a given therapy not having any effect, since the disease may have progressed to a state where the therapy is no longer effective.

A disease is defined as rare (orphan) if it affects fewer than 200,000 people in the US; there are about 7,000 types of such rare disorders. Most of these diseases are genetic, frequently misdiagnosed for years, and without FDA-approved drug treatment. Timely discovery of misdiagnosed and underdiagnosed patients is crucial for their survival and for the proper development and delivery of the right therapeutics (including niche drugs developed by pharmaceutical companies specifically for these rare conditions). The problem of finding potentially undiagnosed subjects for orphan diseases is that active surveillance for such conditions (canvassing a segment of population with questionnaires and/or tests) is expensive and impractical for rare (or even not so rare) diseases, and passive surveillance has to rely on existing medical records (produced by hospitals and insurance companies), which may be incomplete, unreliable, and not contain enough information relevant for the predictive diagnostics. Challenges in identifying these orphan diseases from population-related data exist based on both the limitations of present computing solutions to process the volume of data efficiently and the lack of knowledge regarding what parameters should be searched within this large volume.

One disease that is challenging to diagnose is Hereditary Angioedema (HAE). HAE is a rare genetic condition whose symptoms include swelling in various parts of the body. HAE disease course is episodic in nature with aperiodic episodes. After each episode, the patient recovers fully with no traces left behind. Patients are asymptomatic both before and after attacks and/or episodes of the disease. However, during attacks, patients often suffer excruciating abdominal pain, nausea, and vomiting caused by swelling in the intestinal wall. Swelling of the airway or throat is particularly dangerous, because it can cause death by asphyxiation. Presently, there is a diagnostic test for the disease, but because HAE it is typically misdiagnosed, it is not typically requested by the provider for years prior to diagnosis. The average time to diagnose HAE is seven years and is commonly misdiagnosed as allergic reactions HAE occurs in the US population at a rate ranging from 1 in 10,000 to 1 in 50,000 people.

The challenges related to establishing patterns that identify an event in a large volume of data and actually identifying that event in this large volume are not unique to disease or to orphan disease identification.

SUMMARY OF INVENTION

Shortcomings of the prior art are also overcome and additional advantages are provided through the provision of a method determining a probability of the presence of a given medical condition based on a data set related to a patient, the method includes: obtaining, by one or more processors in a distributed computing environment, one or more machine-readable data sets related to a patient population from one or more databases; identifying, by the one or more processors, based on an initial patient definition, a portion of data from the machine-readable data sets related to a patient population, wherein the portion of the data comprises patients of the patient population with a medical condition; based on a frequency of features in the portion of the data, identifying, by the one or more processors, common features in the portion of the data and weighting the common features based on frequency of occurrence in the portion of the data, wherein the common features comprise mutual information; generating, by the one or more processors, one or more patterns comprising a portion of the common features; generating, by the one or more processors, one or more machine learning algorithms based on the one or more patterns, the one or more machine learning algorithms to identify presence or absence of the given medical condition in an undiagnosed patient based on absence or presence of features comprising the one or more patterns in data related to the undiagnosed patient; utilizing, by the one or more processors, statistical sampling to compile a training set of data, wherein the training set comprises data from the one or more data sets and at least one additional data set comprising data related to a population without the medical condition, and wherein utilizing the statistical sampling comprises formulating and obtaining queries based on the data set and processing and responding to the queries, the processing comprising, for each query: evaluating, by the one or more processors, the query to determine one of a high or a low level of anticipated complexity of a prospective response to the query; based on the query being evaluated at a low level of anticipated complexity, assigning, by the one or more processors, the query to a computing resource in the distributed computing environment, wherein the computing resource is configured to respond to low level complexity queries; and based on the query being evaluated at a high level of anticipated complexity, distributing, by the one or more processors, the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query; tuning, by the one or more processors, the one or more machine learning algorithms by applying the one or more machine learning algorithms to the training set of data; dynamically adjusting, by the one or more processors, the common features comprising the one or more patterns to improve accuracy such that the one or more machine learning algorithms can distinguish patient data indicating the medical condition from patient data that does not indicate the medical condition; and determining, by the one or more processors, based on applying the one or more machine learning algorithms to data related to the undiagnosed patient, a probability, wherein the probability is a numerical value indicating a percentage of commonality between the data related to the undiagnosed patient and the one or more patterns.

Computer systems, computer program products, and methods relating to one or more aspects of the technique are also described and may be claimed herein. Further, services relating to one or more aspects of the technique are also described and may be claimed herein.

Additional features are realized through the techniques of the present invention. Other embodiments and aspects of the invention are described in detail herein and are considered a part of the claimed invention.

BRIEF DESCRIPTION OF DRAWINGS

One or more aspects of the present invention are particularly pointed out and distinctly claimed as examples in the claims at the conclusion of the specification. The foregoing and objects, features, and advantages of one or more aspects of the invention are apparent from the following detailed description taken in conjunction with the accompanying drawings.

DETAILED DESCRIPTION OF THE INVENTION

Figure 1:
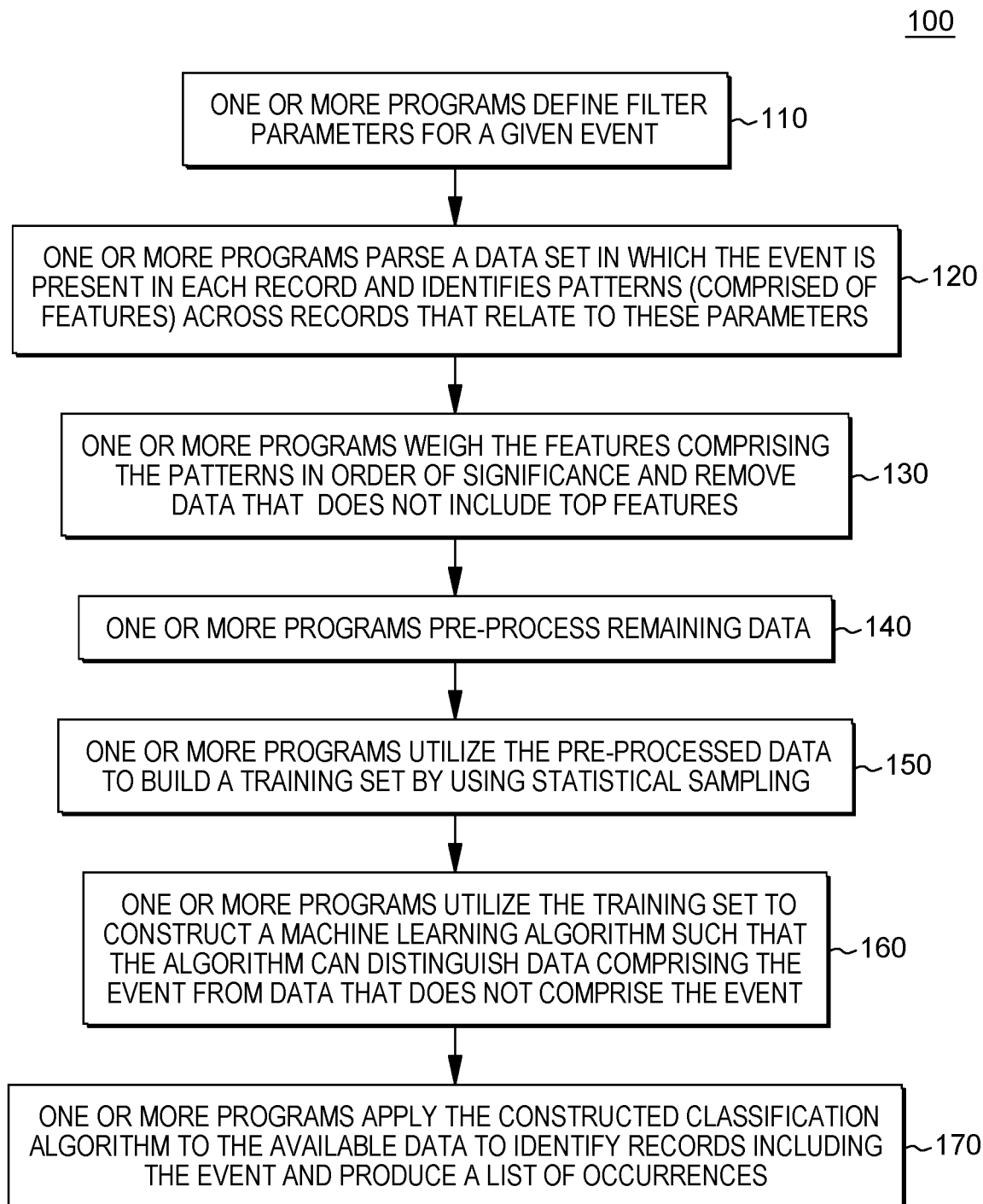
FIG. 1 depicts a workflow associated with aspects of embodiments of the present invention.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure. The terms software, program code, and one or more programs are used interchangeably throughout this application.

The term "diagnose" is utilized throughout the application in to suggest that a data model that is generated and method determining a probability of the presence of a given physical or medical condition, including but not limited to a disease or an orphan disease, based on a data set related to an individual, referred to herein as a patient. However, the so-called diagnosis provided by aspects of embodiments of the present invention is not analogous to a medical diagnosis, provided by a health professional, often based on the result of a medical test or procedure. Rather, a diagnosis herein can be understood as a recognition of a pattern, or a given portion of a pattern, where the pattern was generated as described herein, in embodiments of the present invention. With the specific example of HAE, which is discussed throughout, there is a clinical test that a healthcare provider can utilize to determine whether an individual has HAE. However, the disease is so often misdiagnosed that the test is rarely ordered. Embodiments of the present invention identify previously undiagnosed individuals who may fit a model for the disease that is generated by one or more programs in an embodiment of the present invention. Thus, once identified by the one or more programs in an embodiment of the present invention, a healthcare provider can order the test. Utilizing the test would result in a definitive medical diagnosis. As seen in particular with this example, the one or more programs in an embodiments of the present invention generate a likelihood, while it is a definitive medical test, not the one or more programs, which provide a diagnosis.

Embodiments of the present invention combine data analytics and pattern prediction to enable program code executing on at least one processor to identify patterns within a data set in the absence of advance data defining the pattern. In an embodiment of the present invention, program code analyzes a data set to identify parameters comprising data points characteristic of a certain condition (e.g., a physical condition, a disease, HAE, etc.). The program code adapts a machine learning algorithm to utilize these parameters to identify data consistent with this condition and by utilizing data sets of sizes which cannot be analyzed by a human or by a computing environment that does not adequately distribute processing tasks related to the analysis. The program code identifies these parameters in the absence of established data characterizing the condition. This approach can be utilized to determine recognition patterns to identify diseases (e.g., HAE), including orphan diseases, in a data set that includes data related to individuals with this condition and subsequently, to identify these patterns in an unlimited data set, where the prevalence of individuals with this condition is unknown. However, this approach is not merely limited to physical condition (e.g., disease) identification, but can be utilized in general to predict criteria identifying an event and apply these criteria across a data set that is not constrained by size or complexity. Throughout this specification, aspects of embodiments of the present invention are applied to the task of physical (or medical) condition (e.g., disease) identification, and specifically, to the identification of HAE. However, this singular (non-limiting) application of aspects of embodiments of the present invention is offered to illustrate the functionality of the present invention, as understood by one of skill in the art.

Advantages provided by aspects of some embodiments of the present invention include: (1) the ability to identify features that differentiate individuals with certain medical conditions (e.g., HAE) from the general population, prior to these individuals receiving a formal diagnosis of the medical condition, (2) the ability to determine potential predictors of a future formal diagnosis of a medical condition (e.g., HAE), (3) the ability to demonstrate the appearance of symptoms of the medical condition (e.g., HAE) earlier than currently understood by the medical community, and (4) the ability to provide the potential to accelerate clinical diagnosis of the medical condition (e.g., HAE). In the case where HAE is the condition for which the one or more programs in an embodiment of the present invention generates a model and utilizes the model to identify individuals with a certain probability of future diagnosis, embodiments of the present invention include the following aspects: (1) one or more programs may diagnose patients, on average, approximately 9 to approximately 15 months earlier (with an average of approximately 12 months earlier (than using traditional methods), (2) one or more program may increase the "hit rate" for identifying an individual who is later diagnosed with HAE from 1:10,000 to 1:13, and (3) the one or more programs may geo-locate undiagnosed HAE patients.

The approximate range of 9 to 15 months (averaging 12) is a significant improvement over existing methods of determining whether to implement a test on a patient for HAE that would result in a definitive diagnosis. Using existing techniques, HAE takes a long time from diagnosis to appropriate treatment, generally 8 years. During the 8 years without a diagnosis a patient may frequently visit emergency departments (EDs), be admitted for hospital stays, and often receive inappropriate and expensive procedures. Earlier diagnosis and treatment, which is made possible through the probability determined by program code in embodiments of the present invention, removes patients from the cycle of high-cost, ineffective treatment that drives them back for more of the same, thus reducing waste and improving patient outcomes. It is estimated that there are approximately 3.2 million potential patients with rare diseases in the United States. Thus, by applying predictive analytics to claims databases, the one or more programs identify potential patients with HAE (and other diseases), opening the door for payers to help physicians maximize outcomes and value in the care of these patients.

Certain embodiments of the present invention represent improvements over known methods of data identification, both in the application of identifying individuals with physical/medical conditions, such as HAE, as well as in data management and data mining in general. For example, embodiments of the present invention enable the determination and identification of patterns based on an unlimited number of factors, given the ability of the program code to mine large data stores. For example, when applied to creating a profile (e.g., a disease or medical condition profile) and identifying individuals that fit this profile, relevant features that the program code builds into a pattern for later identification of individuals that fit this pattern are not solely based on diseases, but on drugs and procedures as well, which expands the information content that can be leveraged by the overall process. Embodiments of the present invention increase computational efficiency because, when building a profile to identify a given quality, the program code selects relevant features using not just prior knowledge and frequency count, but ultimate information theory mechanisms, including mutual information, and weight the variety of information utilized by, for example, truncating a the set of obtained features to establish a level of significance for each identified feature in the mutual information.

Mutual information is an example of a method that can be utilized to identify features in an embodiment of the present invention. Further embodiments of the present invention utilize varying techniques to select features, including but not limited to, diffusion mapping, principal component analysis, recursive feature elimination (a brute force approach to selecting features), and/or a Random Forest to select the features. Embodiments of the present invention that utilize mutual information, diffusion mapping, and a Random Forest may provide certain efficiency advantages.

Aspects of embodiments of the present invention represent improvements to existing computing technology and are inextricably tied to computing. Specifically, embodiments of the present invention represent improved methods of handling large volumes of data and for building logistical models from the data. For example, embodiments of the present invention reduce the observed data rate in the eventual results because the program code preprocesses the data utilized to build a pattern, rather than using a less efficient binary binning procedure.

Aspects of embodiments of the present invention are inextricably tied to computing at least because the electronic models, including disease or medical condition models, for conditions such as HAE, generated by embodiments of the present invention cannot be generated outside of computing and do not exist outside of computing. Records initially utilized in embodiments of the present invention are electronic records in one or more data set, contained in one or more database, that are machine readable. The resultant models are also electronic and are applied to additional electronic data sets utilizing computing resources. Because of both the volume and the nature of data, an individual is not capable of accomplishing the specific aspects of embodiments of the present invention that result in a machine readable data model that can be applied by program code to additional data sets in order to identify records with a probability of an event or condition that the model was generated to predict the probable presence of.

Embodiments of the present invention provide utility that individuals and existing systems are incapable of because of the speed at which they are able to provide results. To be useful, program code in embodiments of the present invention both generates and updates models and provides results (identification of records that comport with the model), within a limited temporal period. For example, in a scenario where an individual visits a healthcare provider, the individual and the provider would benefit from acquiring information regarding whether the individual, as represented by an electronic medical record, has items in the record that match the data sought by one or more disease models. If this information cannot be provided within the visit, it is arguably not useful to the individual or the healthcare provider. Thus, in embodiments of the present invention, the program code analyzes an individual record and applies disease models in real-time, or close to real-time. Thus, embodiments of the present invention enable real-time analysis of an electronic medical records of a given individual based on whether the individual's medical records includes one or more patterns determined by program code in embodiments of the present invention.

In certain embodiments of the present invention the program code predicts and detects patterns in data by utilizing Support Vector Machines (SVMs). In an aspect of an embodiment of the present invention, the program code trains a linear SVM classification algorithm for segregating database entries, for example, to separate entries representing individuals with a given condition from entries representing individuals that do not have the condition. In an embodiment of the present invention, the program code utilizes linear SVM, rather than, for example, logistic regression, Random Forest (RF) grouping algorithms, and/or other simple statistical approaches, to achieve a best available classification performance. Another advantage of certain embodiments of the present invention that utilize SVM is that the program code can apply the SVM score of the false positive data as a mechanism to sort out the most promising subjects. (Certain embodiments of the present invention do utilize RF grouping algorithms and logistic regression with SVM in order to achieve hyper-parameter optimization.)

Embodiments of the present invention provide advantages and improvements that are inextricably tied to computer technology also because embodiments of the present invention offer certain advantages that increase computational efficiency and efficacy. For example, as described in greater detail later on, embodiments of the present invention utilize distributed processing based on anticipated query results in order to decrease the timeline for key analytic deliverables. This distributed processing enables the program code to perform multiple analysis processes simultaneously. Portions of certain embodiments of the present invention can be migrated to a cloud architecture and made available to users as software as a service (SaaS) offerings. The unlimited computational capacity of resources in a cloud architecture are suited to support the program code's distribution of simultaneous queries and processes in order to meet the efficiency demands of the system in a data rich environment.

Embodiments of the present invention also provide advantages and improvements that are inextricably tied to computer technology because they utilize machine learning. One advantageous aspect of some embodiments of the present invention over existing approaches to event (e.g., condition) identification in data dense environments is that some other methods approach the problem of event identification and recognition as a statistical problem, instead of a machine learning one, which is an approach that limits the options in available tools. By utilizing machine learning, embodiments of the present invention can identify records that include an event where the information directly identifying the event is absent. For example, by using machine learning, program code can identify patients with a given disease in a data set of undiagnosed patients, i.e., where the data does not already indicate that the disease is present in the patient. In some cases, the program code can utilize machine learning to indicate that an individual is infected with a disease when the opposite is indicated in data related to that individual. Thus, the program code is not merely identifying and retrieving existing established data stored in one or more memory device. Rather, the program code establishes a pattern, continuously trains a machine learning algorithm to apply the pattern, and utilizes the algorithm to identify instances of an event not already explicitly indicated by the data utilizing this pattern.

Embodiments of the present invention provide advantages over known diagnostic systems when utilized to determine mutual information and apply this information to an analysis of a data set where the presence of the event related to the mutual information is unknown, at least because the process is devoid of selection bias. Returning to the disease example, in embodiments of the present invention, there are no assumptions regarding an individual that are carried into the program code and the program code performs its analyses consistently. Selection bias is an issue when attempting to identify a medical condition as a medical professional may be prone to certain conclusions based on, for example, past experience. Expanding on the disease example, this is issue can be problematic both with orphan diseases as well as for diseases for which doctors make a medical diagnosis as a result of eliminating other possibilities. For example, in the area of orphan disease identification, this bias is especially problematic because the rarity of an orphan disease means that a medical professional may come into contact with very few people, or even no people at all, with a given condition until a certain patient presents the condition.

As aforementioned, challenges in identifying conditions, including diseases, such as HAE and various orphan diseases, from population-related data exist based on both the limitations of present computing solutions to process the volume of data efficiently and the lack of knowledge regarding what parameters should be searched within this large volume. In the case of orphan diseases, the small number of confirmed cases renders pattern building and recognition challenging, and the case of a disease where a medical diagnosis is the result of eliminating other possibilities renders the same data problems. In the case of a disease such as HAE, misdiagnosis is so common that ordering a definitive test may not be efficient or effective unless there is some useful information that indicates a probable positive result. Regarding the volume of data, embodiments of the present invention can process a large number of patients coded with a large number of universe codes. For example, an embodiment of the present invention can be utilized to process the patient histories of more than 180 million patients, whose records may include up to 10 years of recorded healthcare history. Given the distributed nature of the processing architecture, the number of patients that can be processed/scored is only limited by storage, as the efficiency of the process enables the processing of increasingly large volumes of data.

Workflows of certain embodiments of the present invention can include three stages: data integration, pattern extraction, and population separation. Data integration refers to aspects of embodiments of the present invention in which the program code derives discriminating features of a first data set, where an event is present. For example, if the event is a certain orphan disease, or HAE, the program code may analyze records of individuals medically diagnosed with the orphan disease or HAE and extract discriminating features that describe the treatment journey of these patients.

Pattern integration refers to aspects of embodiments of the present invention in which the program code develops a pattern for identifying records with a given event based on using the most distinctive features extracted during data integration. For example, the program code would develop patterns describing the most distinctive features of the given disease that the program code extracted from the patient records.

Population separation refers to aspects of embodiments of the present invention where the program code utilizes the pattern to identify the event in one or more data store. For example, returning to the disease example, by analyzing data resources including records identifying large populations, the program code identifies within the resources which patient clusters match the treatment pathways exhibited by the known sufferers.

Referring specifically to HAE, in utilizing aspects of embodiments of the present invention to build a data model related to HAE and applying that dynamic model to identify individuals that fit the model within a given probability, embodiments of the present invention enable identification of early HAE by using big data analytics of a large claims database. FIG. 1 is a workflow 100 that illustrates aspects of embodiments of the present invention, including one or more programs that perform data integration (e.g., patient definition), pattern extraction (e.g., feature extraction), and generate population separation maps (e.g., prediction).

As will be illustrated and discussed herein, one or more programs, executed by at least one processing resource, mine data utilizing various aspects of embodiments of the present invention to identify features in the electronic medical data of patients who were previously medically diagnosed with a given disease. In some embodiments of the present invention, one or more programs in some embodiments of the present invention specifically mine the electronic claim histories of the patients to find factors that differentiate these patients from the general population, even before the patients received the initial diagnosis of HAE by a medical professional.

In at least one embodiment of the present invention one or more programs in embodiments of the present invention determined diagnostic, procedural, therapeutic, and healthcare provider characteristics that were most predictive of a medical diagnosis of HAE. The one or more programs determined that the most predictive diagnoses, in weighted order, include: 1) allergic reactions; 2) swelling, mass, or lump in head and neck; 3) routine general medical examination at a healthcare facility; 4) immunizations and screening for infectious disease; 5) other screening for suspected conditions (not mental disorders or infectious disease); 6) edema; 7) abdominal pain, unspecified site; 8) other upper respiratory disease; 9) unspecified symptom associated with female genital organs; and 10) chronic vascular insufficiency of the intestine. The one or more programs determined that the most predictive procedures include: 1) office or other outpatient visit for the evaluation and management of an established patient; 2) other laboratory; 3) office or other outpatient visit for the evaluation and management of an established patient; 4) laboratory: chemistry and hematology; 5) other therapeutic procedures; 6) pathology; 7) other diagnostic radiology and related techniques; 8) microscopic examination (bacterial smear, culture, toxicology); 9) office or other outpatient visit for the evaluation and management of an established patient; and 10) nonoperative urinary system measurements. The one or more programs determined that the most predictive therapies include: 1) androgens and combinations; 2) blood derivatives; 3) unspecified agents; 4) sympathomimetic agents; 5) adrenals and combinations; 6) analgesics/antipyretics; opiate agonists; 7) antibiotics: penicillins; 8) antibiotics: erythromycin and macrolide; and 9) analgesics/antipyretics; nonsteroidal anti-inflammatory drugs. The one or more programs determined that the most predictive providers include: 1) outpatient hospital; 2) office; 3) independent laboratory; 4) emergency department (hospital); 5) inpatient hospital; 6) independent clinic; 7) patient home; 8) outpatient (not elsewhere classified); 9) ambulatory surgical center; and 10) ambulance (land).

As will be described in more detail below, and as illustrated utilizing FIGS. 1-3, in embodiments of the present invention, one or more programs obtain (exclusively) machine-readable electronic medical records of individuals who were previously medically diagnosed with a disease, such as HAE. The one or more programs analyze (mine) the data utilizing both frequency ranking and by identifying mutual information. Thus, the program code in some embodiments of the present invention employs an analysis that utilizes two data-ranking methods: a frequency method and a mutual information method. The program code utilizes the mutual information measure to quantify the statistical relevance of every feature in the electronic data set(s) of medical records to a future HAE diagnosis. The program code computes the relative frequency of pertinent events to rank the differentiating features based on the mutual information measure. Based on frequency ranking and mutual information, the one or more programs identify distinguishing features in categories that include diagnoses, procedures, drugs, providers, and locations. Based on identifying the distinguishing features, the one or more programs generate predictors (e.g., an adaptive data model), that the one or more programs can apply to data sets where it is unknown whether the individuals represented have HAE, and based on applying the model, the one or more programs can identify probabilities of HAE being present among the individuals represented.

Returning to FIG. 1, FIG. 1 is an example of a workflow 100 of an embodiment of the present invention which includes, as described above, data integration, pattern extraction, and population separation. FIG. 2 provides an overview 200 of portions of FIG. 1, as the aspects of data integration, pattern extraction, and population separation are also illustrated in FIG. 2.

Figure 2:
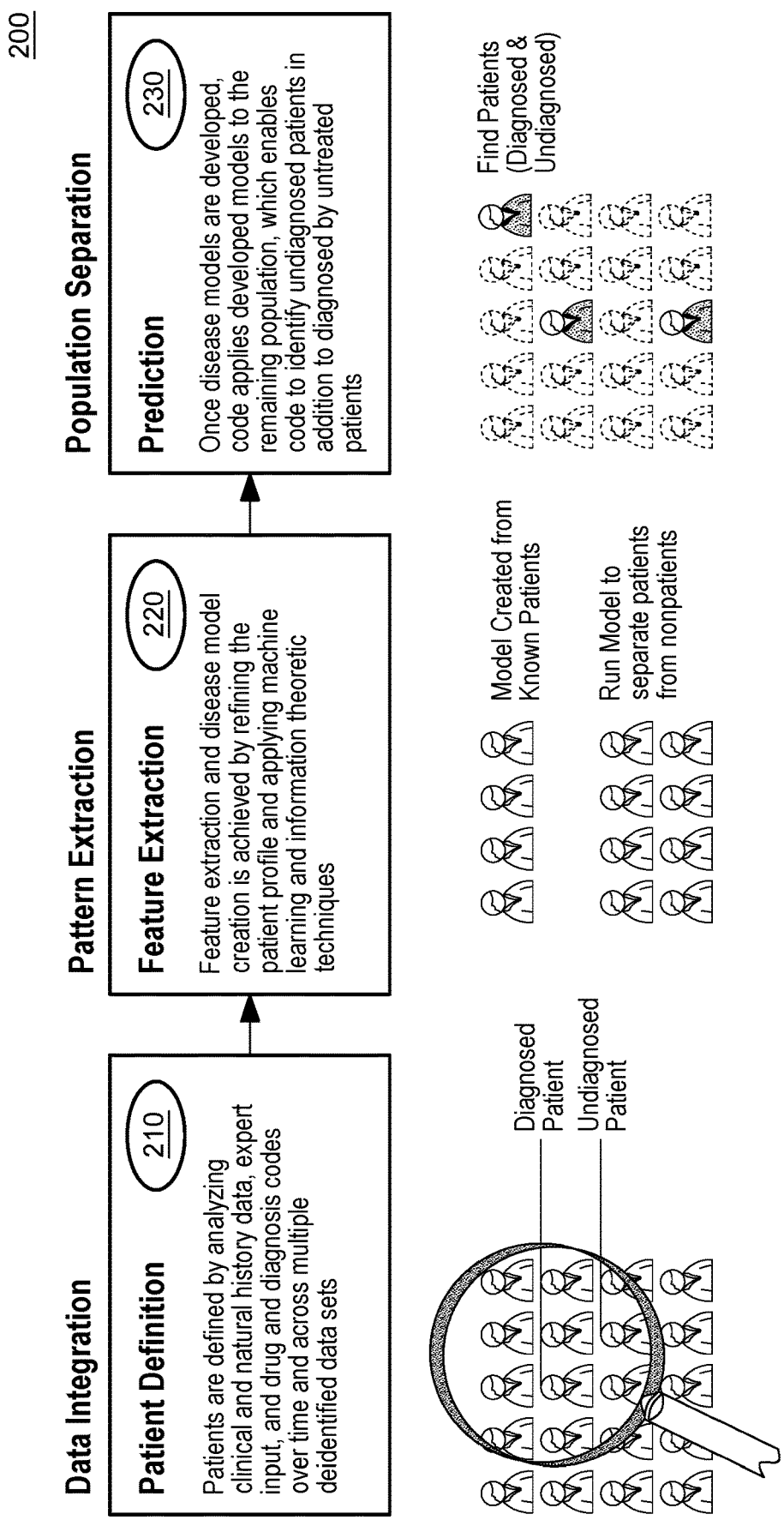
FIG. 2 depicts a workflow associated with aspects of embodiments of the present invention.

As seen in FIG. 2, data integration 210 includes patient definition, where one or more programs generating a patient definition by analyzing electronic records that include, but are not limited to, clinical and natural history data, expert input, and drug and diagnosis codes, over time, and across multiple de-identified data sets. The one or more programs in embodiments of the present invention perform pattern extraction 220, which the one or more programs extract features and create a disease (or event) model creation refining the patient profile and applying machine learning and information theoretic techniques. In population separation 230, the one or more programs make a prediction. Based on the one or more programs completing the development of disease models, the one or more programs applies the developed models to the remaining population, which enables the one or more programs to identify undiagnosed patients, in addition to diagnosed by untreated patients Returning to FIG. 1, in some embodiments of the present invention, the program code defines filter parameters for a given event (110). The filter parameters include data points where patterns could be relevant to the event. For example, if the event is the diagnosis of a given disease, filter parameters may include one or more of disease/diagnostic codes for various comorbid conditions, prescription drugs, inpatient and/or outpatient procedures to diagnose and/or treat symptoms of the disease, visits to specialists, etc. In an embodiment of the present invention, the disease/diagnostic codes may comprise diagnostic codes, such as International Statistical Classification of Diseases and Related Health Problems codes, referred to as ICD-9 codes and the newer ICD-10 codes. In embodiments of the present invention, in order to define a patient with HAE, the one or more programs identified a group of patients in a database (e.g., a medical claims database) who definitely had HAE. As aforementioned, the one or more programs may identify these individuals (who are then utilized to create the patient definition) utilizing diagnosis codes from International Classification of Diseases, Ninth Revision, Clinical Modification (ICD-9-CM). However, in some cases, these codes alone may not be fully reliable for use by the one or more programs because a code may be used for billing purposes without official diagnosis. Also, old codes may be used even after new, more specific codes become available. Also, an ICD-9-CM code sometimes represents a group of diseases. Finally, data entry errors can occur when entering data that one or more programs utilize to create and update the contents of database. In the case of HAE, the one or more programs, in addition to the codes, identified the patients who definitely had the disease by obtaining data (see, e.g., FIG. 9, 910, expert input) indicating that patients prescribed 1 of the 4 HAE-specific drugs available in the United States are patients with HAE. These 4 drugs are Cinryze (C1 esterase inhibitor [human]; Shire), Firazyr (icatibant; Shire), Berinert (C1 esterase inhibitor [human]; CSL Behring), and Kalbitor (ecallantide; Shire). Thus, in the example of building a model to identify HAE, the one or more programs identified patients identified in the database as being prescribed 1 or more of these 4 drugs to form the population of index HAE patients. In one example, the one or more programs identified patients with HAE by searching a medical claims database with the records of over 180 million individuals, ranging in dates from 2006-2014, and identified patients with HAE based on locating all patients prescribed two C1 inhibitors [human] (Cinryze, Berinert), icatibant (Firazyr), and ecallantide (Kalbitor). The identification located 1002 index patients with HAE.

Based on the filter parameters, the program code parses a data set in which the event is present in each record and identifies patterns (comprised of features) across records that relate to these parameters (120). For a HAE, the program code may identify mutual information of all categories of potentially relevant features such as, for example, for comorbid diagnoses, prescription drugs, provider visits, treatment locations, and/or medical procedures. As discussed above, in some embodiments of the present invention, the one or more programs identified mutual information related to diagnosis, procedural, therapeutic, and healthcare provider characteristics, which are enumerated above.

In an embodiment of the present invention, the data set analyzed by the program code comprises medical information (e.g., records) related to a population of individuals with a given disease. For example, the data set may include, coupled with the timing for each feature, diagnostic codes, $D_x(t)$, (e.g., ICD-9 codes, ICD-10 codes), procedures (e.g., Proc(t)), drug treatments, including prescriptions (e.g., Drug (t)), provider visits (Provider(t)), and/or the location(s) of each individual represented in the data set (e.g., Location(t)). Locations may include, but are not limited to, locations of providers who interacted with a patient, a ZIP code related to a practice and/or a patient, a metropolitan area identifier, etc. The constant in the data set is that it is a known that each individual represented by the data has a specific medical condition, including a particular disease. The individual factors or features in the data set can also be referred to collectively as codes.

One or more programs in an embodiment of a present invention may initially identify a population with HAE by electronically isolating a group of records that include individuals definitively diagnosed with the HAE, by utilizing one or more of an ICD-9 code and/or a ICD-10 code specific to HAE, from all patients in the national dataset that includes the electronic medical records of over 180 million patients. In order to further isolate a data set for use in predictive feature analyses (e.g., population separation, FIG. 2, 230), the one or more programs filtered this initial data (110) by identifying, from these electronic records, records that represented individual across all the states in the United States with a minimum of one year of adjudicated claims history prior to the implementation of the diagnosis code for the particular disease in the records.

Referring to FIG. 1 and the example of identifying a pattern for HAE or a given disease, including an orphan disease or other rare disease, in order to identify patterns (e.g., FIG. 1, 120), in an embodiment of the present invention, program code identifies a patient temporal signal, i.e., the codes and the combination of codes that separate individuals with a given condition, for example, from a general population. In an embodiment of the present invention, the program code utilizes feature selection techniques to identify the mutual information in the data set that can be utilized to characterize the given condition. The program code may utilize this mutual information as an inclusion/exclusion index. For example the codes selected through mutual information provide the inclusion criteria for patients to be selected by one or more programs and conversely, those patients who do not possess any of the codes within this set, are excluded by the one or more programs. The goal of feature selection is to define the smallest subset of features that collectively contain most of the mutually shared information and thus most clearly define the characteristics of a patient with a given disease. The one or more programs determined the relative frequency of pertinent events to rank the differentiate features based on the mutual information measure. To build a model for identifying potential individuals to be tested for HAE, the one or more programs in some embodiments of the present invention utilized insurance claims data composed of de-identified diagnosis-related details and payment information. A national claims database utilized to build the model and later to score patients aggregated data for more than 176 million US patients from 2006 to 2014. Claims datasets enable for in-depth assessment of health and quality outcomes when analyzed with tools capable of handling datasets of this size, such as aspects of embodiments of the present invention.

By determining mutual information, the program code in embodiments of the present invention uncovers consistent data over voluminous records that would be impossible outside of the specialized processing, which is discussed herein. In embodiments of the present invention, the program code applies frequency ranking and mutual information procedures to identify the distinguishing features that include diagnoses, procedures, drugs, providers, and locations, which the program code later uses to determine predictors of the HAE. The program code may also take into account feature continuity when determining predictors, as different patterns may emerge within the data at different times. For example, for a given disease, the program code may determine that the occurrence of certain patient features increase over time (e.g., in a 5-year cohort), while certain disorders (e.g., nervous system disorders and other connective tissue disease) increase disproportionately as patients approach diagnosis (by a medical professional), and that other medical conditions (e.g., unspecified diseases of the spinal cord and primary lateral sclerosis) change relatively little over time. In the case of HAE, the one or more programs determined diagnostic, procedural, therapeutic, and healthcare provider characteristics most predictive of HAE.

Using the described analytic methods, the program code identifies features in the claim histories of individuals who were medically diagnosed with HAE, that differentiate these individuals from the general population, before they received the disease diagnosis. For example, the program code determines a group of features or a pattern that is common to these individuals at a time when not enough information was available to the medical professional treating the individuals to make the eventual diagnoses. The program code may determine, for a given disease, that medically significant predictors seen in patients who were eventually diagnosed with the disease include, but are not limited to, nervous system disorders, hereditary and degenerative nervous system conditions, connective tissue disease, skin disorders, lower respiratory disease, gastrointestinal disorders, neurologist visits, orthopedic surgeon visits, gastroenterologist visits, non-traumatic joint disorders, otolaryngologist visits, and the use of certain medications, prior to diagnosis. As is discussed herein, upon identifying the differentiated features, the program code analyzes combinatorial features that differentiate undiagnosed patients from the general population to further characterize early predictors of the disease, and optimize the algorithm differentiating patients with the disease, prior to diagnosis. For HAE, the program code determined that the most predictive diagnoses, in weighted order, include: 1) allergic reactions; 2) swelling, mass, or lump in head and neck; 3) routine general medical examination at a healthcare facility; 4) immunizations and screening for infectious disease; 5) other screening for suspected conditions (not mental disorders or infectious disease); 6) edema; 7) abdominal pain, unspecified site; 8) other upper respiratory disease; 9) unspecified symptom associated with female genital organs; and 10) chronic vascular insufficiency of the intestine. The one or more programs determined that the most predictive procedures include: 1) office or other outpatient visit for the evaluation and management of an established patient; 2) other laboratory; 3) office or other outpatient visit for the evaluation and management of an established patient; 4) laboratory: chemistry and hematology; 5) other therapeutic procedures; 6) pathology; 7) other diagnostic radiology and related techniques; 8) microscopic examination (bacterial smear, culture, toxicology); 9) office or other outpatient visit for the evaluation and management of an established patient; and 10) nonoperative urinary system measurements. The one or more programs determined that the most predictive therapies include: 1) androgens and combinations; 2) blood derivatives; 3) unspecified agents; 4) sympathomimetic agents; 5) adrenals and combinations; 6) analgesics/antipyretics; opiate agonists; 7) antibiotics: penicillins; 8) antibiotics: erythromycin and macrolide; and 9) analgesics/antipyretics; non-steroidal anti-inflammatory drugs. The one or more programs determined that the most predictive providers include: 1) outpatient hospital; 2) office; 3) independent laboratory; 4) emergency department (hospital); 5) inpatient hospital; 6) independent clinic; 7) patient home; 8) outpatient (not elsewhere classified); 9) ambulatory surgical center; and 10) ambulance (land).

Returning to the analysis to generate the predictive model, in embodiments of the present invention, as discussed above, for each category represented in the data set, the program code analyzes items in those categories over time and notes the absence or presence of each item that appears in the data set for each category. Returning to the disease example, in an embodiment of the present invention, the program code separately analyses codes in each of the following categories: $D_x(t)$, Proc(t), Drug(t), Provider(t), Location(t)). The one or more programs considers features including diagnosis codes, procedure codes, medications, standard provider types, and/or standard care facility types.

Table 1 below illustrates an analysis of the program code of the presence and absence of certain items in a given category utilizing the orphan disease identification example. In Table 1, the variables 1 and 0 serve as binary variables and the heading are categorical variable which together represent whether the given item (category) is absent or present at a given time. In the example of Table 1, the diagnosis codes assigned to individuals by medical professionals, in the data set, over time, are analyzed by the program code. In an embodiment of the present invention, the program code repeats this analysis for procedures, drugs, and the locations of the individuals represented in the records in the data set. As is understood by one of skill in the art, program code performing the analysis can identify nuances in the vast data set within a workable timeframe (e.g., during the visit of an individual to a health care provider) based on the utilization of the processing power of the computer system upon which aspects of the present invention are implemented. FIGS. 4-7, which will be discussed herein, include computing configurations that are customized to handle the processing demands that the analysis performed by the program code utilizes

TABLE 1

| Pat(N) | $t_1$ | $t_2$ | $t_3$ | . . . | $t_n$ |
|---|---|---|---|---|---|
| $D_x1$ | 1 | 0 | 1 | | 1 |
| $D_x2$ | 0 | 1 | 0 | | 0 |
| . . . | | | | | |
| $D_xn$ | 1 | 1 | 1 | | 1 |

Referring back to FIG. 1, once the program code has identified patterns, in an embodiment of the present invention, the program code may weigh the features comprising the patterns in order of significance and remove data that do not include top features (130). Embodiments of the present invention employ more than one method of weighing and selecting significant features. As discussed in the HAE example, the program code may rank the features based on the raw mutual information values. However, in some embodiments of the present invention, the program code may view the output of a classifier, e.g., SVM or random forest that will provide a numerical measure of the feature importance that can then be ranked. In an embodiment of the present invention, the program code may weigh a feature with more mutual information across records as more significant. Thus, the program code selects top features (i.e., features with largest values of mutual information, down to the level of significance) from each of the categories and orders them in descending order (according to the values of mutual information). By removing data that does not include top features, the program code focuses the analysis and increases the efficiency in later identifications. The universe of data related to, for example, individuals suffering from an orphan disease, may be extremely vast, and by weighing features of the data, the program code is able to consolidate the data set into a more manageable amount for processing. In an embodiment of the present invention, the program code determines the frequency of a code and represents this frequency with a number between 0 and 1. The program code utilizes these frequency codes to perform binning based on how often each item occurs within the data set.

For ease of understanding, Table 1 displays binary values (1 and 0), however, a data set that is analyzed may include more than one event in a specific time slot, thus, a binary representation, such as Table 1 is not fully representative of this aspect of an embodiment of the present invention and is offered merely for ease of understanding. In fact, for a specific condition or disease, the table would not be binary, but would contain numerical values as the numerical values would represent frequency of a code appearing in a patients' health journey. In an embodiment of the present invention, the values in a matrix can represent the presence or absence of a code in a patient's history (as seen in Table 1), but can also represent the frequency with which the code occurs in that time slot. For example, if each column represents a month, then the numerical value can represent (1) the absence or presence of a code, (2) the number of times that code appears in that time slot, (3) the average frequency with which that code appears in that time slot, and (4) any function that can be applied to the value to represent events in that time slot.

Aspects of embodiments of the present invention utilized to generate mutual information are the same regardless of the condition for which the program code is constructing this information. Thus, embodiments of the present invention are portable over an unlimited number of data sets and can be utilized to identify an unlimited number of events or conditions. As described above, the program code indexes tables in order to derive tables for use in the analysis and, as explained in FIGS. 4-7, the computing is distributed based on the processing demands of the processes performed by the program code to generate the mutual information. In embodiments of the present invention, the program code computes mutual information for each feature as an independent process. The program code computes mutual information a specific feature and an output class variable. Computing the mutual information of two features in separate processes will not affect the result of either computed mutual information result.

Returning to FIG. 1, in an embodiment of the present invention, the program code may pre-process remaining data (140). For example, in an embodiment of the present invention, the program code may use a binning procedure using the average value of the corresponding feature as threshold, for example, values above the threshold are coded as 1, and values below it as 0.

In an embodiment of the present invention, after pre-processing the remaining data, in embodiments where this part of the process is included, the program code utilizes the pre-processed data or access available data sets to build a training set by using statistical sampling (150). The training set includes data representing the event and data that represent an absence of the event. In some embodiments of the present invention, the training set comprises electronic records that are only readable by a computing resource.

The program code formulates the training set by proportionally selecting representative electronic records from the target and control populations: the target population is the population with the condition (e.g., event, disease) and the control population is the population is the negative case (to distinguish from the target). Thus, in the example where an event is a disease, the training set includes disease entries and healthy entries. Departing from the specific disease example, in an embodiment of the present invention, the program code utilizes a test set of training data to train the machine learning algorithm. The training set is selected to include both records with the occurrence or condition the algorithm was generated to identify, and records absent this occurrence or condition. The program code tests/trains the individual features that comprise the mutual information (and/or other technologies discussed herein) selected to identify a given condition, and utilizing voting and ensemble learning, trains the algorithm.

In an embodiment of the present invention, the program code may utilize the training set with the significant patterns identified in the analysis to construct and tune a machine learning algorithm, such that the algorithm can distinguish data comprising the event from data that does not comprise the event (160). The machine learning algorithm may be a linear SVM classification algorithm, which can be utilized with one or more of an RF grouping algorithm and/or a log regression. If the event is a disease, including an orphan disease, the program code may train the machine learning algorithm to separate database entries representing individuals with a disease from entries representing healthy individuals and/or individuals without this particular disease. The program code may utilize the machine learning algorithm, may assign probabilities to various records in the data set during training runs and the program code, may continue training the algorithm until the probabilities accurately reflect the presence and/or absence of a condition in the records within a pre-defined accuracy threshold. With HAE, the program code utilizes a support vector machine (SVM) classifier. The program code made a selection based on a comparative assessment of various classifiers. When building a model for HAE, in some embodiments of the present invention, the program code utilizes Random Forest to generate predictors.

In some embodiments of the present invention, using the disease example, the training set represents a patient population that had the disease. This defined patient population may consist of a constellation of codes, (diagnosis, procedures, drugs, etc.). The machine learning algorithm, which is discussed herein, learns from this defined patient population. In essence, the machine learning algorithm uses a surrogate patient population to find the undiagnosed patients. Stated in another way, the surrogate patient population consists of the patients known to have the disease, and the machine learning algorithms encode their pre-diagnosis characteristics to find similar patients and process the retrospective patient journey to predict the prospective patient journey. In the patient definition process (see, e.g., FIG. 2, 220) the program code identifies cohort of patients that the machine learning algorithm will learn from; this patient cohort will serve as the training set. In embodiments of the present invention, the internal algorithms applied by the program code include, but are not limited to: 1) mutual information to inform or refine the patient definition; and/or 2) various datamining techniques, including but not limited to, histograms to capture procedures, drugs, diagnosis codes, specialty types, geographic location, patient demographics (age, gender), and co-morbidities.

As aforementioned, in an embodiment of the present invention, the program code constructs the machine learning algorithm, which can be understood as a classifier, as it classifies records (which may represent individuals) into a group with a given condition and a group without the given condition. In an embodiment of the present invention, the program code utilizes the frequency of occurrences of features in the mutual information to identify and filter out false positives. The program code utilizes the classifier to create a boundary between individuals with a condition and the general population to lower multi-dimensional planes, given multiple dimensions, including, for example, fifty (50) to one hundred (100) dimensions. When embodiments of the present invention are employed to build a model to predict some HAE, the one or more program employ an ensemble of classifiers developed employing machine learning techniques to optimize the selection and ranking of HAE diagnosis predictors (see, e.g., FIG. 2, 230).

As part of constructing a classifier (machine learning algorithm), the program code may test the classifier to tune its accuracy. In an embodiment of the present invention, the program code feeds the previously identified feature set into a classifier and utilizes the classifier to classify records of individuals based on the presence or absence of a given condition, which is known before the tuning. As aforementioned, the presence or absence of the condition is not noted explicitly in the records of the data set. When classifying an individual with a given condition utilizing the classifier, the program code may indicate a probability of a given condition with a rating on a scale, for example, between 0 and 1, where 1 would indicate a definitive presence. The classifier may also exclude certain individuals, based on the medical data of the individual, from the condition.

In an embodiment of the present invention, the program code constructs more than one machine learning algorithm, each with different parameters for classification, based on different analysis of the mutual information, and generates an ultimate machine learning algorithm based on an aggregation of these classifiers.

In an embodiment of the present invention, to decrease the instances of false positive results, in an embodiment of the present invention, when the algorithm is an SVM algorithm, the program code collects false positive results and sorts them according to their SVM score in order to identify false positives. In an embodiment of the present invention, to increase the comprehensibility and usability of the result, the program code post-processes records identified as including the event according to pre-defined logical filters. These pre-defined filters may be clinically derived (e.g., only males have this disease). In the disease example, the result of applying the classification algorithm is a sorted list of individuals suspected of having the disease.

Departing from the specific disease example and returning to FIG. 1, based on training the machine learning algorithm, the program code applies the constructed classification algorithm to the available data to identify records, including the event, and produces a list of occurrences (170). In some embodiments of the present invention, the constructed classification algorithm is a database object that is stored in a memory resource that is communicatively coupled to the processing resource executing the program code. In some embodiments of the present invention, the list produced is a machine-readable data set that is saved by the program code in stored in a memory resource that is communicatively coupled to the processing resource, including but not limited to, a relational database. As discussed earlier, this process is illustrated in FIG. 2.

Figure 3:
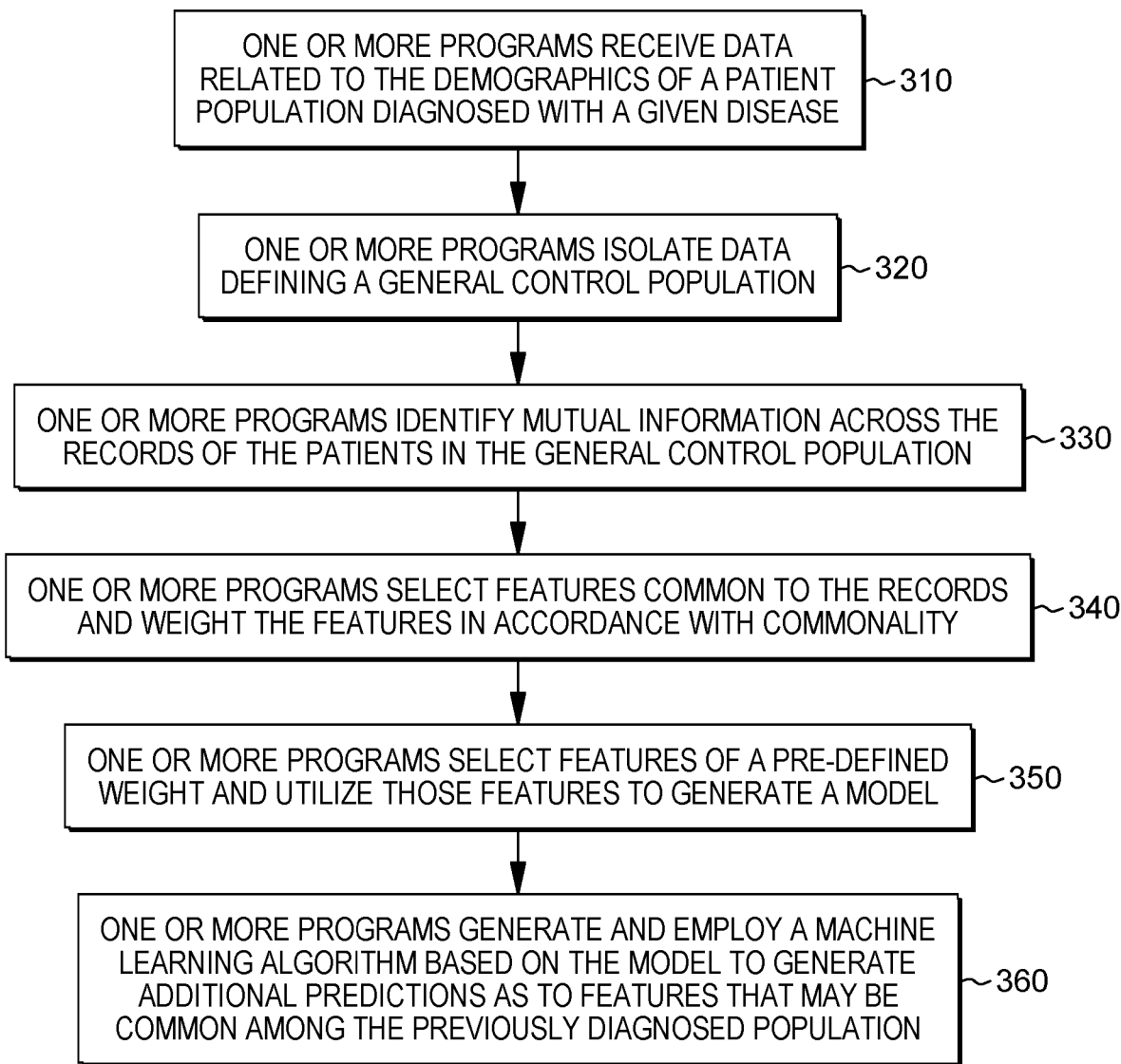
FIG. 3 depicts a workflow associated with aspects of embodiments of the present invention.

FIG. 3 is a workflow 300 of certain aspects of an embodiment of the present invention. In order to offer a comprehensive example of the operation of an embodiment of the present invention, FIG. 3 uses disease identification in population data as an example of the invention's capability in identifying events across one or more data set. Aspects of this workflow 300 are relevant to the specific HAE model disclosed herein. FIG. 3 also demonstrates how the machine learning utilized in the present invention is a continuous process and an evolving process. The training of an algorithm, including but not limited to, an SVM algorithm and/or a random forest algorithm, can be an ongoing and iterative process. For example, the algorithm may include a machine learning algorithm that is continuously trained by the program code as validated samples and their extracted patterns are applied to the training algorithms.

Referring to FIG. 3, the program code receives data related to a patient population diagnosed with a given disease (310). This data is provided in the form of machine-readable electronic medical records. Thus, the program code obtains the data. From the data, the program code isolates data defining a general control population (320). In an embodiment of the present invention, the control population serves as a negative example to the learning algorithm. In addition, the control population can incorporate clinically derived comorbidities to distinguish further the population with the disease from the population without the disease. The program code identifies mutual information across the records of the patients in the general control population (330). The program code selects features common to the records and weighs the features in accordance with commonality (340). The program code selects features of a pre-defined weight and utilizes those features to generate a machine learning algorithm (350). In an embodiment of the present invention, the program code selects features that meet a certain pre-defined threshold based upon the prevalence of the feature in the initial data set. In an embodiment of the present invention, the model defines a group of features for an individual with the disease.

The program code employs the machine learning algorithm to generate additional predictions as to features that may be common among the previously diagnosed population (360). Returning to the example of HAE, the one or more programs in embodiments of the present invention may derive predictors (e.g., diagnosis predictors, see FIG. 2, 230) by differentiating features selected by mutual information and ranking/weighing the features utilizing relative frequency. In some embodiments of the present invention, the one or more programs may generate additional predictions by utilizing data in particular time periods. In building predictors for some diseases, including HAE, the one or more programs in an embodiment of the present invention generate predictors utilizing various time brackets, based on the one or more programs determining that the predictors of a given disease within a data set change over time, with the progression of the disease.

As will be understood by one of skill in the art, patterns or commonalities in the data among various individuals with a given condition may not be readily apparent when the program code scans the data. For this reason, the machine learning algorithm assists the program code in predicting what some commonalities may be, based on already-identified commonalities. The program code can then test whether these predictions represent actual patterns. When a prediction is sufficiently prevalent, the program code updates the pattern and therefore, the machine learning algorithm, to include this quality.

The identification of features, generation of a model, and generation of prediction for additional features, is an iterative process that tunes the machine learning algorithm that the program code ultimately utilizes to identify undiagnosed patients in an expanded data set. Additionally, the program code can utilize features derived from one data set in an analysis of another data set. Thus, based on the predictions, the program code selects features common to the records and weighs the features in accordance with commonality (340). The program code selects features of a pre-defined weight and utilizes those features to update the model (350). Thus, the machine learning aspect of an embodiment of the present invention is iterative.

As demonstrated in FIG. 3, not only does the program code train a machine learning algorithm based on weighted mutual information initially identified by the program code upon obtaining and/or receiving the data, the algorithm also generates predictions for data that may exist in the data set that was not initially identified, enabling the program code to further analyze the data based in these predictions, validate or invalidate the predictions, and based on this result, further train the algorithm to improve its ability to identify, for example, undiagnosed patients with a given disease.

Returning to FIG. 3, the program code applies the machine learning algorithm to identify undiagnosed individuals with a disease in a larger population (360).

In an embodiment of the present invention, the program code can align the determination of a diagnosis for a given individual with the timing of the diagnosis as related to items in the mutual information that match up with the data related to the individual.

An important challenge of identifying an isolated event in a data set utilizing a machine learning algorithm that can utilize unlimited parameters of varying complexity is that the computation can be extremely inefficient, as the algorithms scale non-linearly. Thus, when the program code trains and applies the machine learning algorithm to identify undiagnosed individuals with a disease in a larger population (360), in embodiments of the present invention, the queries utilized in the training and application of the algorithm are distributed to increase the efficiency of the process. Specifically, in an aspect of certain embodiments of the present invention, the program code receives queries throughout the process of identifying the events in the data set and evaluates the complexity of the queries before assigning a computer resource to answer the query. For example, in an embodiment of the present invention, the program code decides where to route a query based on the complexity of the anticipated answer to the query. In this manner, the program code sends a straightforward database query that can be answered with a single value pulled from a data set in response to a resource configured to respond efficiently to this type of query. Meanwhile, queries that require more complex responses, such as queries included in the execution of the machine learning algorithm, may be distributed over a group of resources to maximize efficiency, without compromising functionality.

In an embodiment of the present invention, the program code builds and improves the model through machine learning at a granular level. The model building code architecture is integrated in the sense that the only input needed is a list of patient IDs (de-identified patient ID numbers), and a list of features to include in the model. The model builder sets up the testing and training sets, extracts the appropriate retrospective patient histories from the database and builds a suite of models, optimizes them, ensembles them and then generates a report on their performance.

In an embodiment of the present invention, a database comprises a set of tables that are derived from the raw data obtained from the claims data vendor. This new data architecture combines the relevant data elements from all the "raw" tables and produces tables that contain only the pertinent information used for the machine learning models. The tables are indexed (internal database optimization) so that queries execute faster. In embodiments of the present invention, the program code derives a set of population tables from the raw tables, extracting data elements pertinent and representative of each patient's health journey. The extracted data includes, for each record, the diagnosis code, the date, the patient id number, the drug code, the procedure code, and all matched to the date on the claim. In embodiments of the present invention, separate tables exist for the diagnosis code, drugs code, procedure code, and the specialty type.

Figure 4:
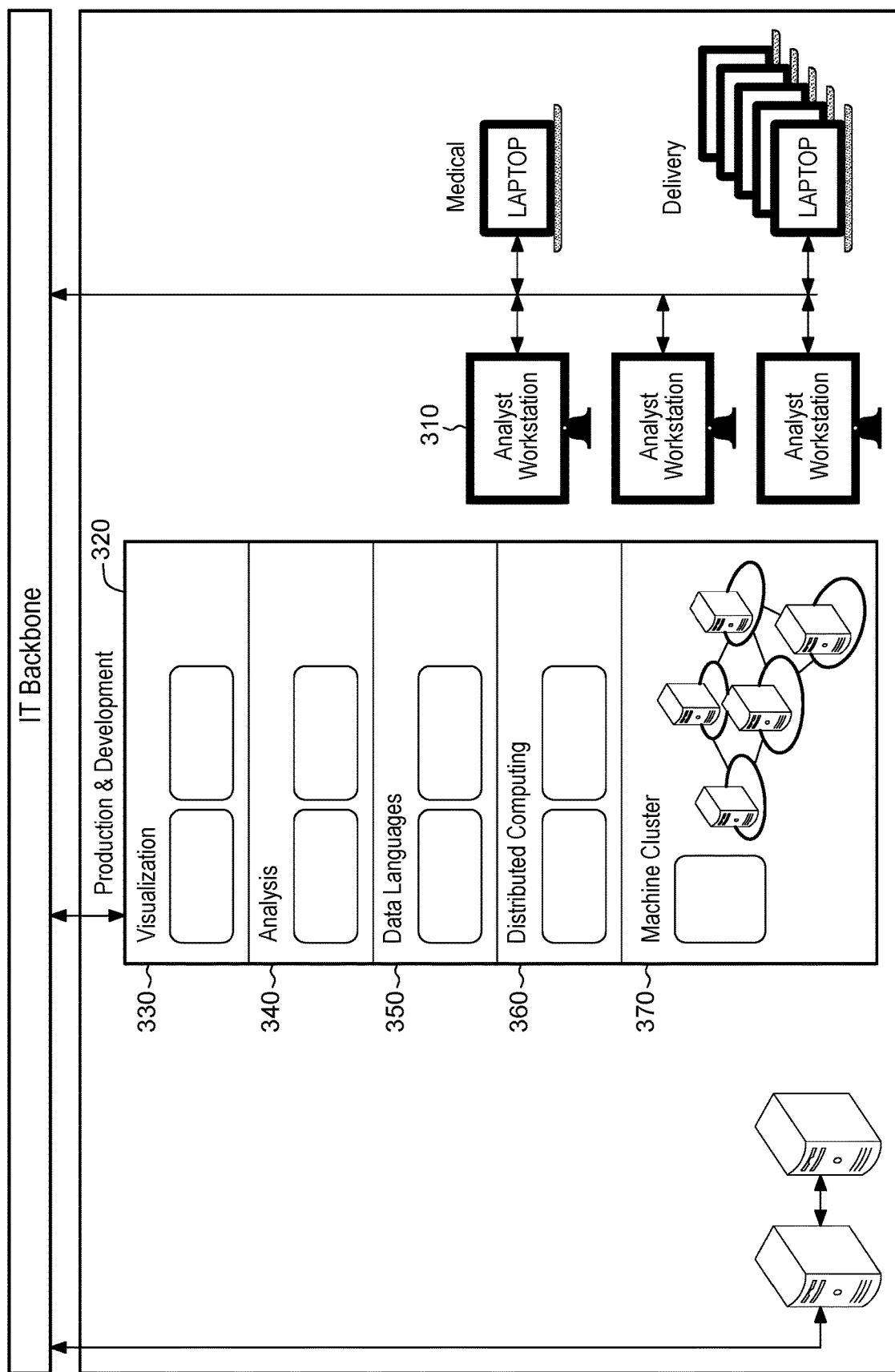
FIG. 4 depicts one example of aspects of a computing environment used to execute one or more aspects of an embodiment of the present invention.

FIG. 4 depicts a technical architecture that may be utilized by an embodiment of the present invention. In an embodiment of the present invention, a user utilizes a workstation 310 to connect to a distributed computing environment 320 over a network connection. The network utilized can be wired, wireless or hybrid and may be public or private, depending upon the data security employed in the delivery of the data. The network may include the Internet. The distributed computing environment is layered in order to service efficiently the queries and machine learning of the method. Layers includes a visualization layer 330 responsible for delivery of comprehensive results, an analysis layer 340 responsible for processing and responding to queries that require straightforward data access answers, a data language layer 350 to extract, transform, load, generate derived tables to increase efficiency, extract and prepare data for machine learning algorithms, and/or apply information theoretic techniques to extract all features, and a distributed computing layer 360 responsible for allocating resources for processing various threads utilized in embodiments of the present invention. The program code in the distributed computing layer 360 manages at least one server 370 (the cluster of five servers in FIG. 4 is merely one example used to illustrate and is not limiting). The distributed computing layer 360 receives each query and/or instruction and the program code in the distributed computing layer decides, based on the type of response the query requests or the complexity of the instruction, whether to distribute the query or instruction to a resource in of the managed resources 370 and to which resource the query/instruction should be distributed.

Figure 5:
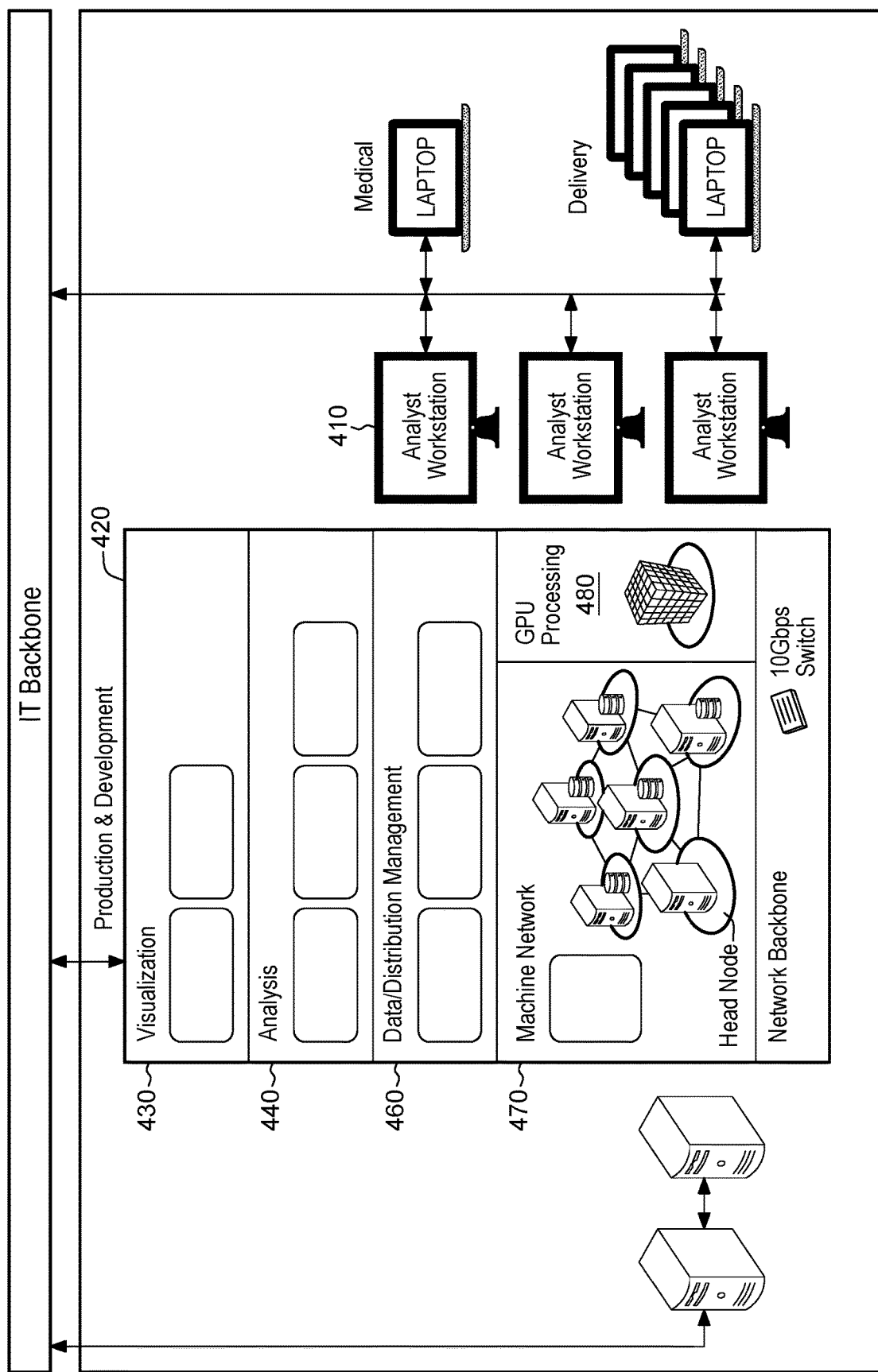
FIG. 5 depicts one example of aspects of a computing environment used to execute one or more aspects of an embodiment of the present invention.

FIG. 5 depicts another architecture that can be utilized by embodiments of the present invention. In this technical environment, rather than a data languages layer, a combined data/distribution management layer 460 layer manages distribution to the managed resources 470, as well as to at least one dedicated processing resource 480, which handles the machine learning. This dedicated processing resource 480 can handle multiple threads simultaneously. At the data/distribution management layer, the program code receives a query and based on the type of response the query is requesting, the program code decides whether to distribute the query to the managed resources 470 or to answer the query with the resource in the data/distribution management layer 460. In embodiments of the present invention, general database queries are handled by resources at the data/distribution management layer 460 without further distribution. In addition, the distributing functionality, program code executing on resources in the data/distribution management layer 460 also interact with the dedicated processing resource to select the parameters utilized in the machine learning.

Figure 6:
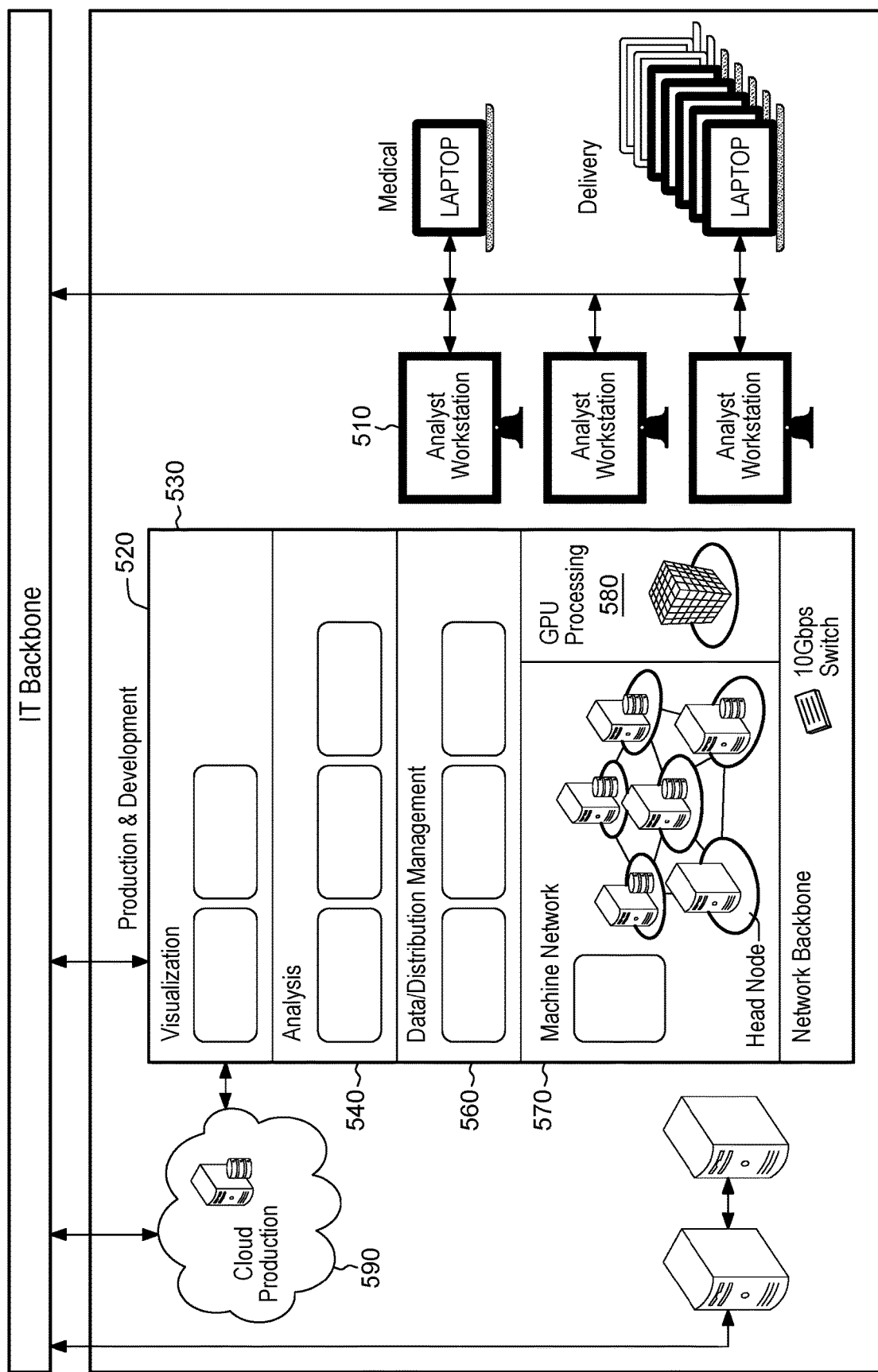
FIG. 6 depicts one example of aspects of a computing environment used to execute one or more aspects of an embodiment of the present invention.

FIG. 6 is one example of a computing environment utilized by some embodiments of the present invention that includes elements of a cloud 590. In this example, the program code utilizes the resource of the cloud 590 to pre-populate data at rest so that the data utilized by the program code in the present invention both to train the machine learning algorithm and ultimately to identify records with a given event (e.g., disease) is unlimited. Aspects of certain embodiments of the present invention can be deployed as SaaS utilizing this cloud 590 environment.

Figure 7:
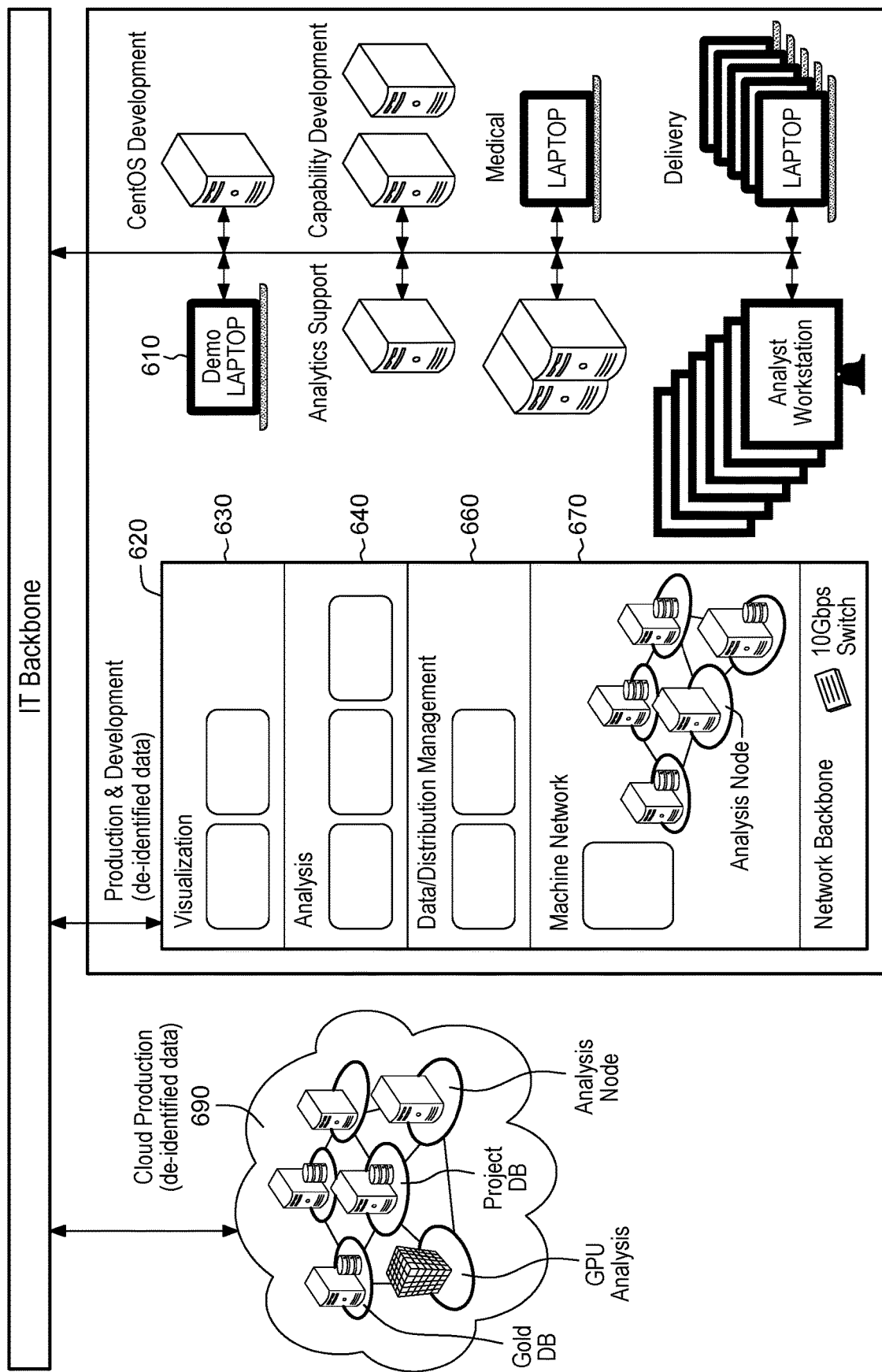
FIG. 7 depicts a workflow associated with aspects of embodiments of the present invention.

FIG. 7 is another example of a technical environment that can be a portion of an embodiment of the present invention. In this example, as with FIG. 6, the present invention that includes elements of a cloud 590. In this example, as with FIG. 6, the program code utilizes the resource of the cloud 590 to pre-populate data at rest so that the data utilized by the program code in the present invention both to train the machine learning algorithm and ultimately to identify records with a given event (e.g., disease) is unlimited. Aspects of certain embodiments of the present invention can be deployed as SaaS utilizing this cloud 590 environment. Utilizing the technical architecture of this figure, program code will execute: (1) on the 5 machine network, and/or (2) on AWS cloud computing infrastructure.

Figure 8:
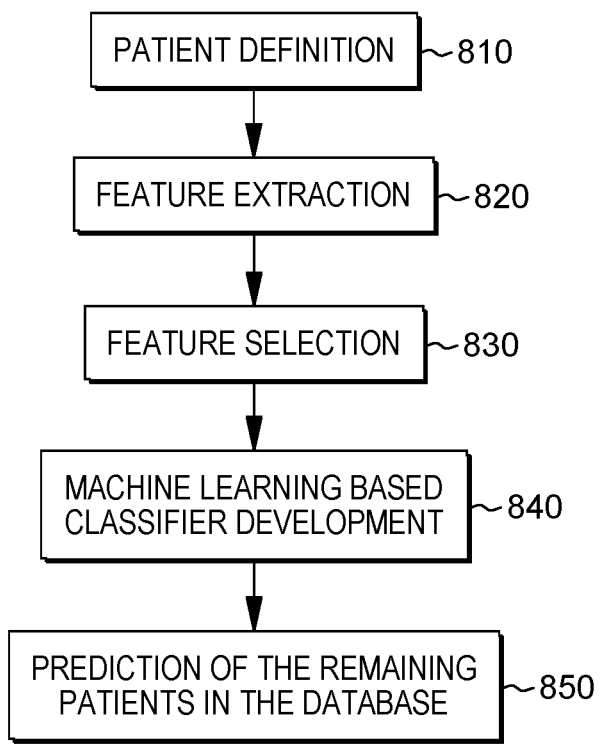
FIG. 8 depicts one example of aspects of a computing environment used to execute one or more aspects of an embodiment of the present invention.

FIG. 8 is a general workflow 800 that illustrates aspects of various aspects of some embodiments of the present invention. This workflow 800 provides a general guide to certain features of embodiments of the present invention. Each aspect of this workflow 800 is performed by program code executed by at least one processing circuit. As illustrated in FIG. 8, the program code performs patient definition 810, feature extraction 820, feature selection 830, machine learning based classifier development 840, and prediction of the remaining patients in the database 850.

The application of certain aspects of embodiments of the present invention to the identification of diseases can be understood in the context of the example that follows. Below, for HAE, data related to the demographics of a patient population diagnosed with HAE was obtained by one or more programs from a database of de-identified patient claims data acquired from an insurance claims database. For example, a database utilized in an embodiment of the present invention may comprise data covering eight years. An embodiment of the present invention was utilized to discover patients within this database who had not yet been diagnosed with HAE. The description is genericized in order to illustrate the functionality.

Stage 1: Patient Definition (e.g., FIG. 2, 210; FIG. 8. 810)

In order to identify individuals with HAE in the database to utilize in order to ultimately identify other individuals, the one or more programs define a HAE patient by utilizing information in the records related to ICD-9 and certain HAE-specific drugs, here referred to as Drug 1, Drug 2, and Drug 3. This set of patients is referred to as the "gold standard" HAE group. For example, the patient definition used for HAE may consist of the ICD-9 and ICD-10 diagnosis codes along with the relevant drugs. The program code may apply a set of definitions, which may include or exclude drugs. In some embodiments of the present invention, the definition applied by the one or more programs may also include or exclude related conditions, along with a specific repeatability that the one or more programs identify by observing the codes.

Stage 2: Model Creation (e.g., FIG. 2, 220; FIG. 8. 820-840)

In order to identify which features or combination of features are most statistically relevant for differentiating HAE from non-HAE patients, an information-theoretical concept of mutual information was utilized to determine the differentiating features. As discussed earlier, mutual information is a measure of how much information about one set of data can be determined from another set of data. Features or their combinations with higher mutual information values are likely to be more informative for discriminating HAE from non-HAE patients.

After the program code determines the mutual information of individual features or their combinations, the program code begins feature selection. The goal of feature selection is to define the smallest subset of features that collectively contain most of the mutually shared information and thus most clearly define the characteristics of the HAE patient. As discussed above, machine learning algorithms drive the analysis of feature selection that created a model of HAE. Thus, the program code generates a model consisting of the fewest possible and simultaneously most differentiating characteristics of the HAE patients, resulting in an enhanced patient definition.

Stage 3: Prediction (e.g., FIG. 2, 230; FIG. 8. 850)

Once the program code determines a model of the characteristics of the HAE patient from the gold standard HAE patients, the program code scores the remaining population of patients in the data set by the model to find undiagnosed patients. In order to score patients, the program code computes the features for every patient in the data set not in the set of gold HAE patients. Each patient's features (or characteristics) were input by the program code to the HAE computer model and the program code produced a numerical score. This numerical score is the likelihood that the patient is an undiagnosed HAE patient. The numerical score can be used to rank patients from those who are most likely to be undiagnosed with HAE to those that are least likely to have HAE. As discussed above, embodiments of the present invention are designed to handle an unlimited amount of data, thus, in building and applying models and later, making predictions based on the model, the program code has generated scores for over 180 million patients without temporal delays. The prioritized list may be used to allocate resources to address the needs of the highest likely patients.

In an embodiment of the present invention, once the one or more programs generated a model based on determining the characteristics of the patient with HAE from the index patients with HAE, the one or more programs scored the remaining population of patients in the data set, utilizing the model, to find undiagnosed patients. For, the one or more programs determine features that did not appear in the set of index patients with HAE. The one or more programs obtain each patient's features and input these features into the HAE model. The result of the one or more programs applying the model to the features is a numerical score that represents the likelihood that the patient had undiagnosed HAE. In an embodiment of the present invention, the one or more programs rank the identified patients, based upon the assigned scores, from most likely to least likely to have the condition.

In an embodiment of the present invention, the training set is processed dynamically and informs and tunes the model and the data of unknown patients is continually utilized to tune the model. For example, during the building phase of the model, the output of the model with a training set input, is compared to a known label (patient with disease or not) (supervised learning). The error is used to modify the internal parameters of the model. This process continues until the error is minimized. However, once the model is built, it is then used to score the patients. For each patient (e.g., of the at least 180 million), the features are computed and fed through the model. The output of the model indicates whether the patient is a likely undiagnosed disease patient or not. (The output is binary.)

Stage 4: Validating HAE Patients

There are at least two approaches considered to validate that the predicted undiagnosed HAE patients actually have the condition in various embodiments of the present invention. The first approach is to perform a field validation, where the appropriate personnel are deployed at providers to educate them on the characteristics of potential HAE patients. The providers would then call in those patients and get them tested for HAE. This process could take several months. An alternative approach is to monitor the health claims of the predicted patients over time. As the healthcare claims data is updated (monthly), the program code flags new HAE patients with a definitive diagnosis indication. In this manner the number of predicted undiagnosed patients that are validated to have the disease can be determined without engaging the sales force or medical science liaisons. In addition how far ahead in time the prediction was made before the true diagnosis can be determined.

In some embodiments of the present invention, included in the electronic records is provider information associated with each patient represented, as well as the patient's claims. Thus, if the one or more programs scores a patient as having a likelihood of a disease within a certain threshold, the one or more programs may electronically notify the provider of this result.

The information identified by the program code and incorporated in the model may include age, gender, diagnosis codes, procedures, prescriptions, provider types, and facility types. As discussed above, program code in an embodiment of the present invention may store the resultant model in a database and continually update/tune the model as the repeated application provides more intelligence.

Figure 9:
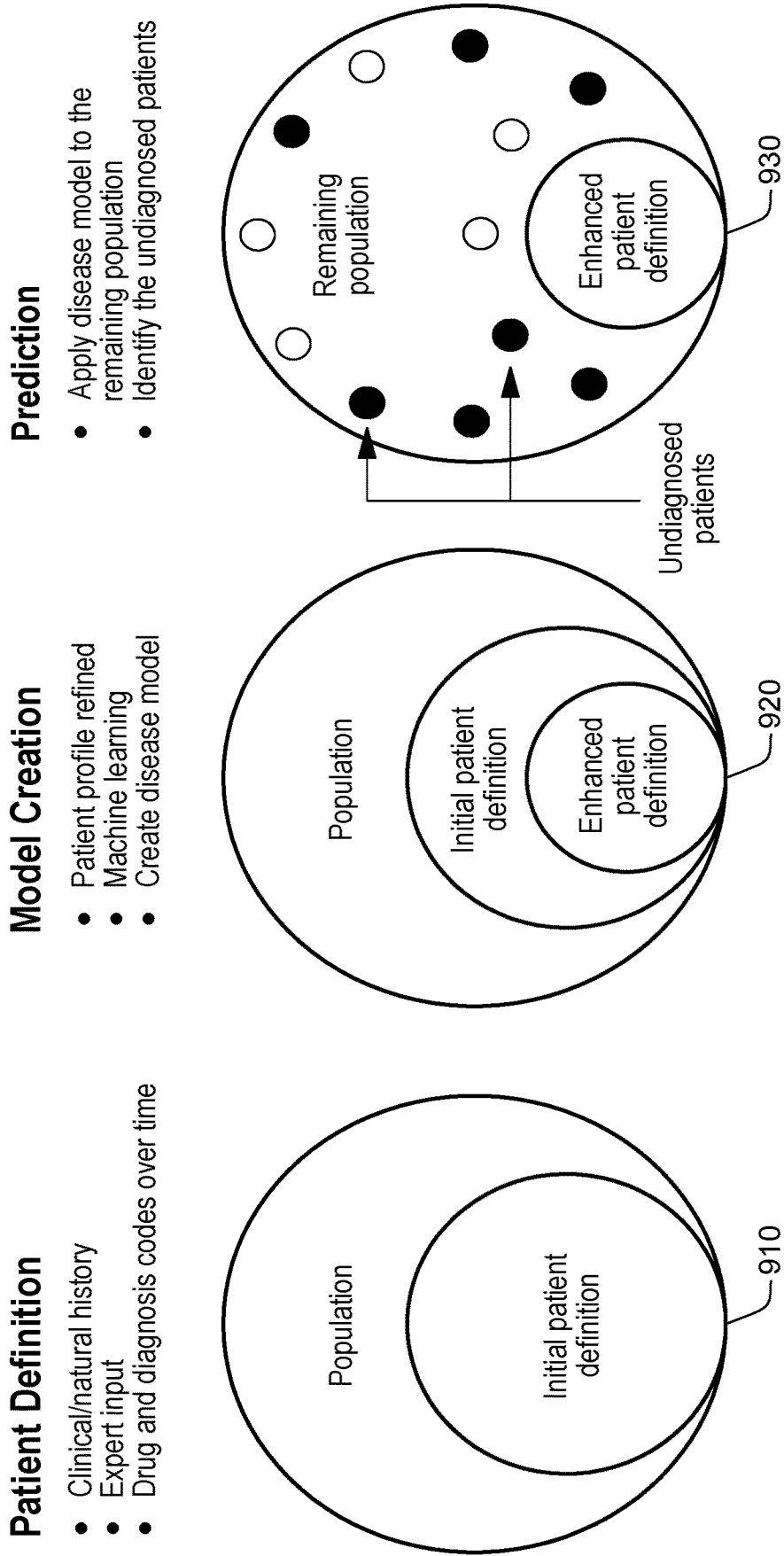
FIG. 9 illustrates certain aspects of some embodiments of the present invention.

FIG. 9 illustrates various aspects of some embodiments of the present invention. In this example, embodiments of the present invention utilize electronic medical records (including those from a claims database) as inputs, but also utilize additional information in order to define a patient population. As illustrated in FIG. 9, one or more programs in an embodiment of the present invention analyzes clinical/natural history, expert input, and drug and diagnosis codes over time, in order to determine an initial patient definition 910 for a given disease. As illustrated in FIG. 9, the individuals the program code differentiates the individuals who fit the initial patient definition that it determines from a general population, all of whom are represented electronically in at least one database. The patient definition 910 can be understood as the statistical "signature" of the given disease. In some embodiments of the present invention, the program code analyzes diagnosis codes from International Classification of Diseases, Ninth Revision, Clinical Modification (ICD-9-CM) to build the patient definition. However, in the event that these codes, alone, do not produce a definitive definition, due to the coding code the records being unreliable (e.g., without official diagnosis; old codes may be used even after new, more specific codes become available, an ICD-9-CM code sometimes represents a group of diseases, and/or data entry errors have occurred), additional information may be utilized. With certain diseases, drugs prescribed to patients before diagnosis are indicators of an eventual diagnosis. Additionally, certain embodiments of the present invention may request and receive user inputs when building the patient definition. During the patient definition building process, the one or more programs may prompt the user, through a graphical user interface, for additional input. For example, the one or more programs may recognize a trend with certain drugs and may pose a question to the user regarding how to weight this factor in building the definition.

The one or more programs generate a model 920 of the disease by refining the initial patient profile through machine learning to generate a disease model. As illustrated in FIG. 9, the individuals in a population who fit the enhanced disease definition in a subset of individual that fit the initial definition, which is a subset of the total population. To identify which features or combination of features are most statistically relevant for differentiating patients with a certain disease from patients without this disease, in some embodiments of the present invention, the program code utilizes mutual information to determine the differentiating features. As discussed above, mutual information is a measure of how much information about one set of data can be determined from another set of data. The features with higher mutual information values are likely to be more informative for discriminating patients with a given disease from those without the given disease. After the program code determined the mutual information of individual features or their combinations, the program code begins to select features to define the smallest subset of features that collectively contain most of the mutually shared information and thus most clearly define the characteristics of the patient with the disease. The program code utilizes machine-learning algorithms to drive the analysis of feature selection to create the model. Thus, the model generated by the program code in an embodiment of the present invention includes the fewest possible and simultaneously most differentiating characteristics of patients with the given disease, resulting in the pictured enhanced patient definition.

The one or more programs predict which individuals of a remaining population have a relevant probability of being diagnosed with the disease 930. The one or more programs apply disease model to the remaining population in order to identify individuals who may be diagnosed with the disease in the future, based on matching the disease model to a relevant degree. As seen in FIG. 9, the undiagnosed patients are a subset of the remaining population. As illustrated, once the program code generated a model of the characteristics of the patient with a given disease from the index patients with the given disease, the program code utilized the model to score the remaining population of patients in the data set to find undiagnosed patients. For every remaining patient in the data set, the program code computes the features that did not appear in the set of index patients with the disease. The program code inputs each patient's features in the model, which produces a numerical score. This score represents the likelihood that the (undiagnosed) patient has the disease. In some embodiments of the present invention, the program code ranks the patients from most likely to least likely to have the condition.

Figure 10:
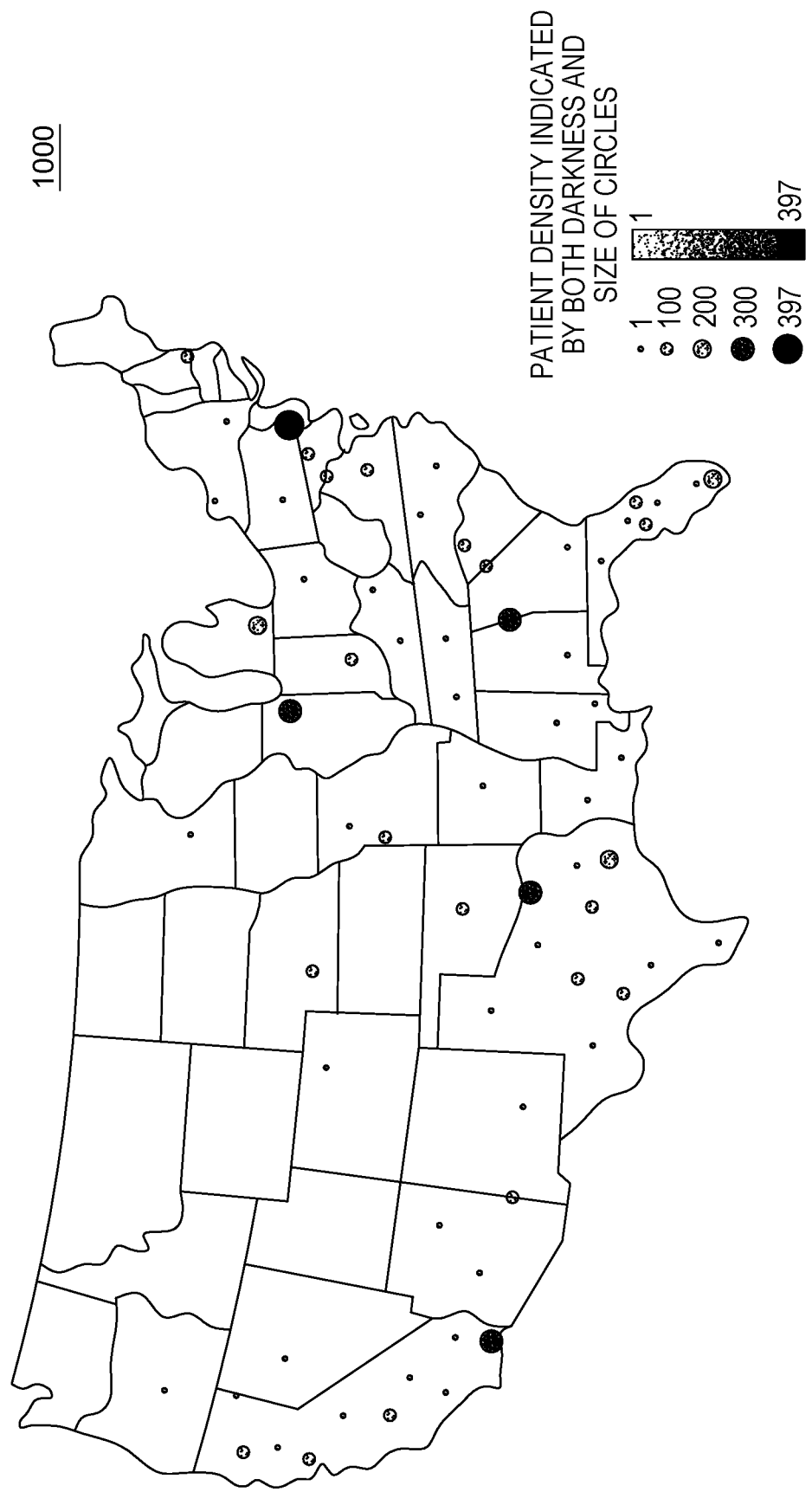
FIG. 10 depicts a distribution of potential Hereditary Angioedema (HAE) patients within metropolitan statistical areas as determined by certain aspects of some embodiments of the present invention.

FIG. 10 depicts a distribution of potential HAE patients within metropolitan statistical areas as determined by certain aspects of some embodiments of the present invention. The one or more programs made this determination is this example utilizing data from 2006-2014 where N=5511. To predict (e.g., FIG. 9, 930) a model of the HAE patient's history and profile, the one or more programs apply the enhanced patient definition determined during model creation (e.g., FIG. 9, 920) to the remaining population of patients in the database (or more than one database). The one or more programs set the prediction classifier set to a detection probability (e.g., probability >0.8) and apply the model to the remaining population. Based on this application of the model, the one more programs determine that there are N (5511) potentially undiagnosed patients with HAE in the database. In some embodiments of the present invention, although the data in the database is de-identified (see, e.g., FIG. 7, 690), the patient information in the database is linked to metropolitan statistical areas (MSAs), which enables the one or more programs to deliver its results in a manner that includes the geographic distribution of the information. The Office of Management and Budget defines MSAs for use by federal statistical agencies. The distribution of the predicted HAE patients across the United States, as predicted by the one or more programs in an aspect of certain embodiments of the present invention, is depicted in the map 1000 in FIG. 10.

Some embodiments of the present invention include a computer-implemented method, a computer system, and a computer program product where one or more programs in a distributed computing environment, one or more programs obtain one or more machine-readable data sets related to a patient population from one or more databases. The one or more programs identify, based on an initial patient definition, a portion of data from the machine-readable data sets related to a patient population, wherein the portion of the data comprises patients of the patient population with a medical condition. Based on a frequency of features in the portion of the data, the one or more programs identify common features in the portion of the data and weighting the common features based on frequency of occurrence in the portion of the data, wherein the common features comprise mutual information. The one or more programs generate one or more patterns comprising a portion of the common features. The one or more programs generate one or more machine learning algorithms based on the one or more patterns, the one or more machine learning algorithms to identify presence or absence of the given medical condition in an undiagnosed patient based on absence or presence of features comprising the one or more patterns in data related to the undiagnosed patient. The one or more programs utilize statistical sampling to compile a training set of data, wherein the training set comprises data from the one or more data sets and at least one additional data set comprising data related to a population without the medical condition, and wherein utilizing the statistical sampling comprises formulating and obtaining queries based on the data set and processing and responding to the queries, the processing comprising, for each query. The one or more programs evaluate the query to determine one of a high or a low level of anticipated complexity of a prospective response to the query. Based on the query being evaluated at a low level of anticipated complexity, the one or more programs assign the query to a computing resource in the distributed computing environment, wherein the computing resource is configured to respond to low level complexity queries. Based on the query being evaluated at a high level of anticipated complexity, the one or more programs distribute the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query. The one or more programs tune the one or more machine learning algorithms by applying the one or more machine learning algorithms to the training set of data. The one or more programs dynamically adjust the common features comprising the one or more patterns to improve accuracy such that the one or more machine learning algorithms can distinguish patient data indicating the medical condition from patient data that does not indicate the medical condition. The one or more programs determine, based on applying the one or more machine learning algorithms to data related to the undiagnosed patient, a probability, wherein the probability is a numerical value indicating a percentage of commonality between the data related to the undiagnosed patient and the one or more patterns.

In some embodiments of the present invention, the initial patient definition is selected from the group consisting of: a pre-defined diagnosis code and a pre-defined medication.

In some embodiments of the invention, the pre-defined medication is selected from the group consisting of: Cinryze, Firazyr, Berinert, and Kalbitor, and the probability indicates a probability that the undiagnosed patient has the medical condition.

In some embodiments of the invention, the one or more machine-readable data sets comprise the data related to the undiagnosed patient.

In some embodiments of the invention, the one or more programs determine, based on applying the one or more machine learning algorithms to data related to each patient not included in the portion of the data, for each patient, a respective probability, wherein the respective probability is a numerical value indicating the percentage of commonality between the data related to the undiagnosed patient and the one or more patterns.

In some embodiments of the invention, the one or more programs rank the probability and the respective probabilities, in order of relevance and notify, through an electronic communication, a user of an identity of any patient in the one or more machine-readable data sets with a probability above a predetermined threshold. The one or more programs automatically order, based on communicating with an order management system over a network connection, a clinical test for the medical condition, wherein a number of tests ordered is directly proportional to a number of patients with the probability above the predetermined threshold In some embodiments of the invention, the generating the one or more patterns by the one or more programs includes: ranking, by the one or more processors, the common features based on the weighting; and retaining, by the one or more processors, the portion of the common features wherein the portion comprises common features of a pre-defined weight, wherein the portion comprises the one or more patterns.

In some embodiments of the invention, the mutual information comprises features from a plurality of feature categories and wherein each pattern of the one or more patterns comprising a portion of the common features comprises features in one feature category of the plurality of feature categories.

In some embodiments of the invention, the medical condition is Hereditary Angioedema, and wherein the one feature category is selected from the group consisting of: diagnosis codes, procedures, therapies, providers, and locations.

In some embodiments of the invention, the feature category is diagnosis codes and a feature is selected from the group consisting of: an allergic reaction, swelling, mass, or lump in head and neck, routine general medical examination at a healthcare facility, immunizations and screening for infectious disease, other screening for suspected conditions that are not mental disorders or infectious diseases, edema, abdominal pain at an unspecified site; another upper respiratory disease, unspecified symptom associated with female genital organs, and chronic vascular insufficiency of the intestine.

In some embodiments of the invention, the feature category is procedures and a feature is selected from the group consisting of: an office or other outpatient visit for the evaluation and management of an established patient, another laboratory procedure, an office or other outpatient visit for the evaluation and management of an established patient, a chemistry and hematology laboratory procedure, another therapeutic procedure, a pathology procedure, another diagnostic radiology and related technique, a microscopic examination, an office or other outpatient visit for evaluation and management of an established patient, and a nonoperative urinary system measurement.

In some embodiments of the invention, the feature category is therapies and a feature is selected from the group consisting of: androgens and combinations, blood derivatives, androgens and combinations, unspecified agents, sympathomimetic agents, adrenals and combinations, analgesics or antipyretics that are opiate agonists, antibiotics that are penicillins, antibiotics that are erythromycin and macrolide, and analgesics or antipyretics that are nonsteroidal anti-inflammatory drugs.

In some embodiments of the invention, the feature category is providers and a feature is selected from the group consisting of: an outpatient hospital, an office, an independent laboratory, an emergency department, an inpatient hospital, an independent clinic, a patient home, an outpatient location that is not elsewhere classified, an ambulatory surgical center; and a land ambulance.

In some embodiments of the invention, the one or more machine learning algorithms comprise a linear Support Vector Machines classification algorithm.

In some embodiments of the invention, the one or more machine learning algorithms comprise at least two machine learning algorithms and wherein the tuning further comprises the one or more programs compiling results of the tuning of each of the at least two machine learning algorithms and utilizing ensemble learning to consolidate portions of the at least two machine learning algorithms into a single machine learning algorithm.

In some embodiments of the invention, the tuning the one or more programs includes the one or more programs associating, based on applying the one or more machine learning algorithms to the training set of test data, probabilities to a portion of the records in the training set of test data, wherein the probabilities reflect a likelihood of presence of the medical condition for each record training set of test data. The one or more programs complete the dynamically adjusting of the common features when the probabilities are within a pre-defined accuracy threshold.

In some embodiments of the invention, the one or more programs determine the probability by obtaining, from a computing resource, electronic medical records for the undiagnosed patient for a defined temporal period, wherein the electronic medical records comprise electronic contact information for a healthcare provider to the undiagnosed patient. The one or more programs apply the one or more machine learning algorithms to the electronic medical records. The one or more programs determine, based on the applying, if the probability is within a predetermined range. Based on determining that the probability exceeds a predetermined threshold, the one or more programs electronically alert, in real time, the healthcare provider to the undiagnosed patient of the probability.

In some embodiments of the invention, the one or more programs retain, in a memory resource communicatively coupled to the one or more processors, the one or more patterns. The one or more programs obtain an indication regarding accuracy of the probability. The one or more programs update the one or more patterns based on the indication.

Figure 11:
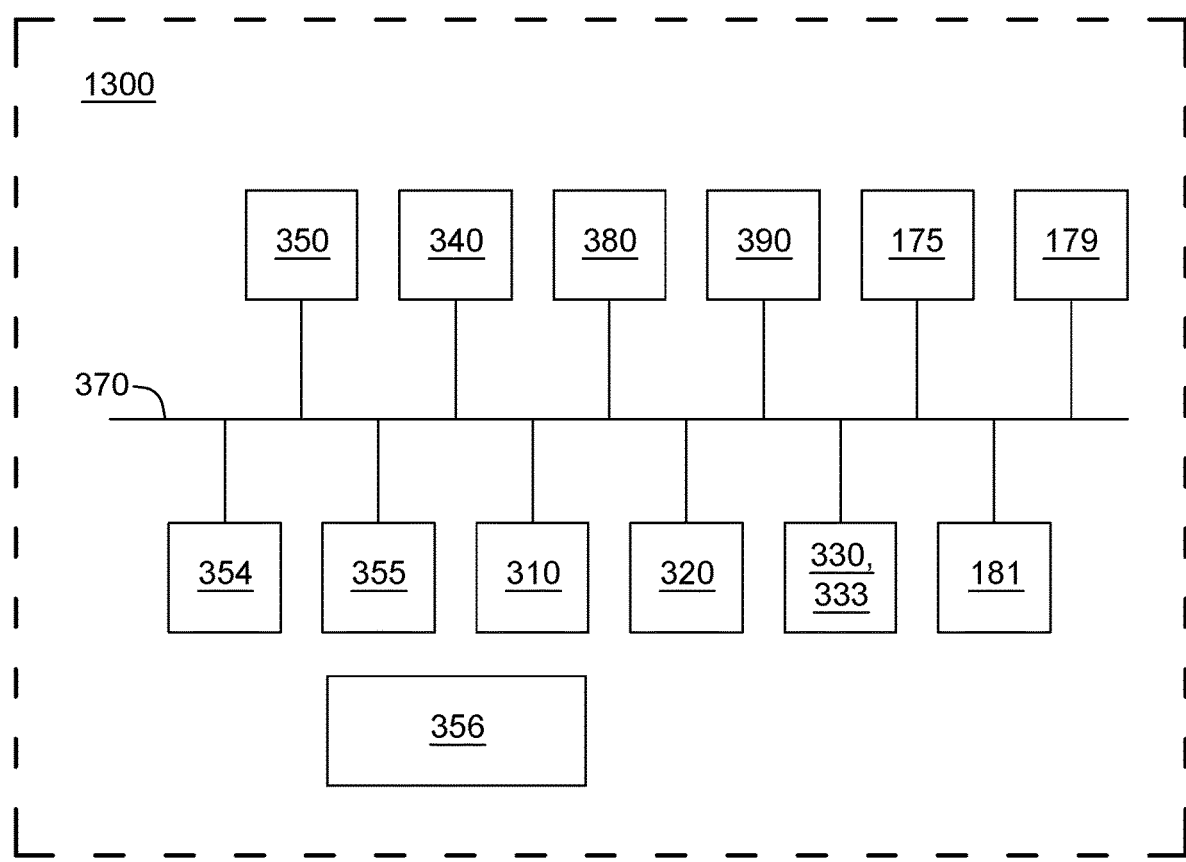
FIG. 11 depicts one embodiment of a single processor computing environment, which may comprise a node of a cloud computing environment, to incorporate and use one or more aspects of the present invention.

FIG. 11 illustrates a block diagram of a resource 1300 in computer system 110 and/or terminal 120a-120b, which is part of the technical architecture of certain embodiments of the technique. The resource 1300 may include a circuitry 370 that may in certain embodiments include a microprocessor 354. The computer system 1300 may also include a memory 355 (e.g., a volatile memory device), and storage 181. The storage 181 may include a non-volatile memory device (e.g., EPROM, ROM, PROM, RAM, DRAM, SRAM, flash, firmware, programmable logic, etc.), magnetic disk drive, optical disk drive, tape drive, etc. The storage 355 may comprise an internal storage device, an attached storage device and/or a network accessible storage device. The system 1300 may include a program logic 330 including code 333 that may be loaded into the memory 355 and executed by the microprocessor 356 or circuitry 370.

In certain embodiments, the program logic 330 including code 333 may be stored in the storage 181, or memory 355. In certain other embodiments, the program logic 333 may be implemented in the circuitry 370. Therefore, while FIG. 2 shows the program logic 333 separately from the other elements, the program logic 333 may be implemented in the memory 355 and/or the circuitry 370.

Using the processing resources of a resource 1300 to execute software, computer-readable code or instructions, does not limit where this code can be stored.

Figure 12:
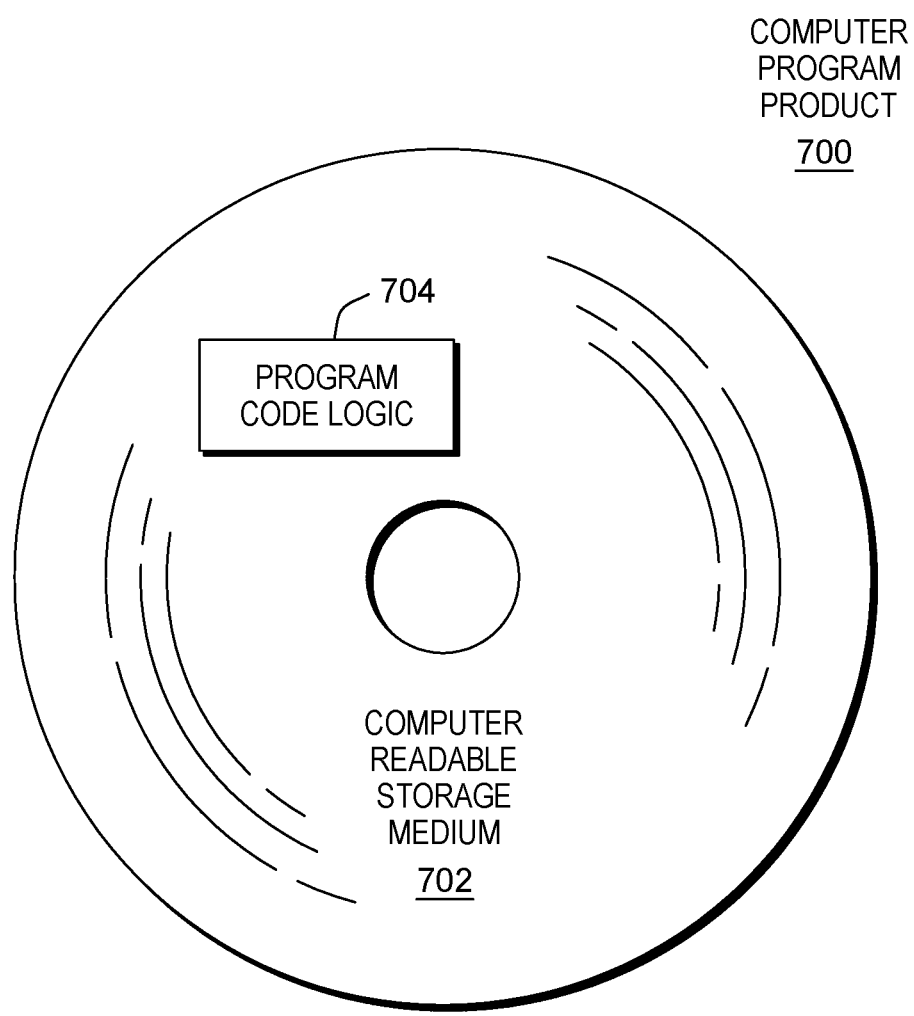
FIG. 12 depicts one embodiment of a computer program product incorporating one or more aspects of the present invention.

Referring to FIG. 12, in one example, a computer program product 700 includes, for instance, one or more non-transitory computer readable storage media 702 to store computer readable program code means or logic 704 thereon to provide and facilitate one or more aspects of the technique.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including an object oriented programming language, such as Java, Smalltalk, Java, Python, R-Language, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions, also referred to as computer program code, may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In addition to the above, one or more aspects of the technique may be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider may receive payment from the customer under a subscription and/or fee agreement, as examples. Additionally or alternatively, the service provider may receive payment from the sale of advertising content to one or more third parties.

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique. As a further aspect of the technique, the system can operate in a peer to peer mode where certain system resources, including but not limited to, one or more databases, is/are shared, but the program code executable by one or more processors is loaded locally on each computer (workstation).

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

Embodiments of the present invention may be implemented in cloud computing systems. FIG. 6 may also comprise a node in this type of computing environment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method, comprising:

obtaining, by one or more processors in a distributed computing environment, one or more machine-readable data sets related to a patient population from one or more databases;

identifying, by the one or more processors, based on an initial patient definition, a portion of data from the machine-readable data sets related to the patient population, wherein the portion of the data comprises patients of the patient population with an orphan disease, wherein the orphan disease is Hereditary Angioedema, and wherein the one feature category is selected from the group consisting of: diagnosis codes, procedures, therapies, providers, and locations;

based on a frequency of features in the portion of the data, identifying, by the one or more processors, common features in the portion of the data and weighting the common features based on frequency of occurrence in the portion of the data, wherein the common features comprise mutual information, wherein the mutual information comprises features from a plurality of feature categories and wherein each pattern of the one or more patterns comprising a portion of the common features comprises features in one feature category of the plurality of feature categories;

utilizing, by the one or more processors, the mutual information to update the initial patient definition, to generate an enhanced patient definition, wherein generating the enhanced patient definition comprises:

identifying, by the one or more processors, one or more features of the common features with mutual information values above a predefined threshold; and selecting, by the one or more processors, a portion of the common features, wherein the portion of the common features comprises a smallest subset of features from the one or more features that collectively contain a majority of the mutual information, wherein the portion of the common features comprises the enhanced patient definition, and wherein the portion of the common features comprises a smallest number of the common features that is a largest number of differentiating characteristics of the patient population diagnosed with the orphan disease;

generating, by the one or more processors, one or more patterns comprising the portion of the common features;

generating, by the one or more processors, one or more machine learning algorithms based on the one or more patterns, the one or more machine learning algorithms to identify presence or absence of the given orphan disease in an undiagnosed patient based on absence or presence of features comprising the one or more patterns in data related to the undiagnosed patient;

utilizing, by the one or more processors, statistical sampling to compile a training set of data, wherein the training set comprises data from the one or more data sets and at least one additional data set comprising data related to a population without the orphan disease, and wherein utilizing the statistical sampling comprises formulating and obtaining queries based on the data set and processing and responding to the queries, the processing comprising, for each query:

evaluating, by the one or more processors, the query to determine if a prospective response to the query is a single value pulled from a single data set;

based on determining that the prospective response to the query is the single value pulled from the single data set, assigning, by the one or more processors, the query to a given computing resource in the distributed computing environment; and based on determining that the prospective response to the query, distributing, by the one or more processors, the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query;

tuning, by the one or more processors, the one or more machine learning algorithms by applying the one or more machine learning algorithms to the training set of data;

dynamically adjusting, by the one or more processors, the common features comprising the one or more patterns to improve accuracy such that the one or more machine learning algorithms can distinguish patient data indicating the orphan disease from patient data that does not indicate the orphan disease; and determining, by the one or more processors, based on applying the one or more machine learning algorithms to data related to the undiagnosed patient, a probability, wherein the probability is a numerical value indicating a percentage of commonality between the data related to the undiagnosed patient and the one or more patterns, wherein the probability indicates a probability that the undiagnosed patient will be diagnosed with the orphan disease in the future.

2. The method of claim 1, wherein the initial patient definition is selected from the group consisting of: a pre-defined diagnosis code and a pre-defined medication.

3. The method of claim 1, wherein the one or more machine-readable data sets comprise the data related to the undiagnosed patient.

4. The method of claim 3, further comprising:
determining, by the one or more processors, based on applying the one or more machine learning algorithms to data related to each patient not included in the portion of the data, for each patient, a respective probability, wherein the respective probability is a numerical value indicating the percentage of commonality between the data related to the undiagnosed patient and the one or more patterns.

5. The method of claim 4, further comprising:
ranking, by the one or more processors, the probability and the respective probabilities, in order of relevance; and
notifying, by the one or more processors, through an electronic communication, a user of an identity of any patient in the one or more machine-readable data sets with a probability above a predetermined threshold; and
automatically ordering, by the one or more processors, based on communicating with an order management system over a network connection, a clinical test for the orphan disease, wherein a number of tests ordered is directly proportional to a number of patients with the probability above the predetermined threshold.

6. The method of claim 1, wherein the generating the one or more patterns comprises:
ranking, by the one or more processors, the common features based on the weighting; and
retaining, by the one or more processors, the portion of the common features wherein the portion comprises common features of a pre-defined weight, wherein the portion comprises the one or more patterns.

7. The method of claim 1, wherein the pre-defined medication is selected from the group consisting of: Cinryze, Firazyr, Berinert, and Kalbitor.

8. The method of claim 7, wherein the feature category is diagnosis codes and one of the features is selected from the group consisting of: an allergic reaction, a swelling, mass, or lump in head and neck, a routine general medical examination at a healthcare facility, an immunization and screening for an infectious disease, another screening for suspected conditions that are not mental disorders or infectious diseases, an edema, an abdominal pain at an unspecified site, another upper respiratory disease, an unspecified symptom associated with female genital organs, and a chronic vascular insufficiency of the intestine.

9. The method of claim 7, wherein the feature category is procedures and one of the features is selected from the group consisting of: an office or other outpatient visit for the evaluation and management of an established patient, another laboratory procedure, an office or other outpatient visit for the evaluation and management of an established patient, a chemistry and hematology laboratory procedure, another therapeutic procedure, a pathology procedure, another diagnostic radiology and related technique, a microscopic examination, an office or other outpatient visit for evaluation and management of an established patient, and a nonoperative urinary system measurement.

10. The method of claim 7, wherein the feature category is therapies and one of the features is selected from the group consisting of: androgens and combinations, blood derivatives, androgens and combinations, unspecified agents, sympathomimetic agents, adrenals and combinations, analgesics or antipyretics that are opiate agonists, antibiotics that are penicillins, antibiotics that are erythromycin and macrolide, and analgesics or antipyretics that are nonsteroidal anti-inflammatory drugs.

11. The method of claim 7, wherein the feature category is providers and one of the features is selected from the group consisting of: an outpatient hospital, an office, an independent laboratory, an emergency department, an inpatient hospital, an independent clinic, a patient home, an outpatient location that is not elsewhere classified, an ambulatory surgical center; and a land ambulance.

12. The method of claim 1, wherein the one or more machine learning algorithms comprise a linear Support Vector Machines classification algorithm.

13. The method of claim 1, wherein the one or more machine learning algorithms comprise at least two machine learning algorithms and wherein the tuning further comprises:
compiling results of the tuning of each of the at least two machine learning algorithms and utilizing ensemble learning to consolidate portions of the at least two machine learning algorithms into a single machine learning algorithm.

14. The method of claim 1, the tuning further comprising:
associating, by the one or more processors, based on applying the one or more machine learning algorithms to the training set of test data, probabilities to a portion of the records in the training set of test data, wherein the probabilities reflect a likelihood of presence of the orphan disease for each record training set of test data; and
completing the dynamically adjusting of the common features when the probabilities are within a pre-defined accuracy threshold.

15. The method of claim 1, wherein the determining the probability comprises:
obtaining, by the one or more processors, from a computing resource, electronic medical records for the undiagnosed patient for a defined temporal period, wherein the electronic medical records comprise electronic contact information for a healthcare provider to the undiagnosed patient;
applying, by the one or more processors, the one or more machine learning algorithms to the electronic medical records;

determining, by the one or more processors, based on the applying, if the probability is within a predetermined range; and based on determining that the probability exceeds a predetermined threshold, electronically alerting, in real time, the healthcare provider to the undiagnosed patient of the probability.

16. The method of claim 15, further comprising:

retaining, by the one or more processors, in a memory resource communicatively coupled to the one or more processors, the one or more patterns;

obtaining, by the one or more processors, an indication regarding accuracy of the probability; and updating, by the one or more processors, the one or more patterns based on the indication.

17. A computer program product comprising:

a non-transitory computer readable storage medium readable by one or more processors in a distributed computing environment, and storing instructions for execution by the one or more processors for performing a method comprising:

obtaining, by the one or more processors in a distributed computing environment, one or more machine-readable data sets related to a patient population from one or more databases;

identifying, by the one or more processors, based on an initial patient definition, a portion of data from the machine-readable data sets related to the patient population, wherein the portion of the data comprises patients of the patient population with an orphan disease, wherein the orphan disease is Hereditary Angioedema, and wherein the one feature category is selected from the group consisting of: diagnosis codes, procedures, therapies, providers, and locations;

based on a frequency of features in the portion of the data, identifying, by the one or more processors, common features in the portion of the data and weighting the common features based on frequency of occurrence in the portion of the data, wherein the common features comprise mutual information, wherein the mutual information comprises features from a plurality of feature categories and wherein each pattern of the one or more patterns comprising a portion of the common features comprises features in one feature category of the plurality of feature categories;

utilizing, by the one or more processors, the mutual information to update the initial patient definition, to generate an enhanced patient definition, wherein generating the enhanced patient definition comprises:

identifying, by the one or more processors, one or more features of the common features with mutual information values above a predefined threshold; and selecting, by the one or more processors, a portion of the common features, wherein the portion of the common features comprises a smallest subset of features from the one or more features that collectively contain a majority of the mutual information, wherein the portion of the common features comprises the enhanced patient definition, and wherein the portion of the common features comprises a smallest number of the common features that is a largest number of differentiating characteristics of the patient population diagnosed with the orphan disease;

generating, by the one or more processors, one or more patterns comprising the portion of the common features;

generating, by the one or more processors, one or more machine learning algorithms based on the one or more patterns, the one or more machine learning algorithms to identify presence or absence of the given orphan disease in an undiagnosed patient based on absence or presence of features comprising the one or more patterns in data related to the undiagnosed patient;

utilizing, by the one or more processors, statistical sampling to compile a training set of data, wherein the training set comprises data from the one or more data sets and at least one additional data set comprising data related to a population without the orphan disease, and wherein utilizing the statistical sampling comprises formulating and obtaining queries based on the data set and processing and responding to the queries, the processing comprising, for each query:

evaluating, by the one or more processors, the query to determine if a prospective response to the query is a single value pulled from a single data set;

based on determining that the prospective response to the query is the single value pulled from the single data set, assigning, by the one or more processors, the query to a given computing resource in the distributed computing environment; and based on determining that the prospective response to the query, distributing, by the one or more processors, the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query;

tuning, by the one or more processors, the one or more machine learning algorithms by applying the one or more machine learning algorithms to the training set of data;

dynamically adjusting, by the one or more processors, the common features comprising the one or more patterns to improve accuracy such that the one or more machine learning algorithms can distinguish patient data indicating the orphan disease from patient data that does not indicate the orphan disease; and determining, by the one or more processors, based on applying the one or more machine learning algorithms to data related to the undiagnosed patient, a probability, wherein the probability is a numerical value indicating a percentage of commonality between the data related to the undiagnosed patient and the one or more patterns, wherein the probability indicates a probability that the undiagnosed patient will be diagnosed with the orphan disease in the future.

18. A system comprising:

one or more memory;

one or more processors in communication with the memory; and program instructions executable by the one or more processors in a distributed computed environment via the one or more memory to perform a method, the method comprising:

obtaining, by the one or more processors in a distributed computing environment, one or more machine-readable data sets related to a patient population from one or more databases;

identifying, by the one or more processors, based on an initial patient definition, a portion of data from the machine-readable data sets related to the patient population, wherein the portion of the data comprises patients of the patient population with an orphan disease, wherein the orphan disease is Hereditary Angioedema, and wherein the one feature category is selected from the group consisting of: diagnosis codes, procedures, therapies, providers, and locations;

based on a frequency of features in the portion of the data, identifying, by the one or more processors, common features in the portion of the data and weighting the common features based on frequency of occurrence in the portion of the data, wherein the common features comprise mutual information, wherein the mutual information comprises features from a plurality of feature categories and wherein each pattern of the one or more patterns comprising a portion of the common features comprises features in one feature category of the plurality of feature categories;

utilizing, by the one or more processors, the mutual information to update the initial patient definition, to generate an enhanced patient definition, wherein generating the enhanced patient definition comprises:

identifying, by the one or more processors, one or more features of the common features with mutual information values above a predefined threshold; and selecting, by the one or more processors, a portion of the common features, wherein the portion of the common features comprises a smallest subset of features from the one or more features that collectively contain a majority of the mutual information, wherein the portion of the common features comprises the enhanced patient definition, and wherein the portion of the common features comprises a smallest number of the common features that is a largest number of differentiating characteristics of the patient population diagnosed with the orphan disease;

generating, by the one or more processors, one or more patterns comprising the portion of the common features;

generating, by the one or more processors, one or more machine learning algorithms based on the one or more patterns, the one or more machine learning algorithms to identify presence or absence of the given orphan disease in an undiagnosed patient based on absence or presence of features comprising the one or more patterns in data related to the undiagnosed patient;

utilizing, by the one or more processors, statistical sampling to compile a training set of data, wherein the training set comprises data from the one or more data sets and at least one additional data set comprising data related to a population without the orphan disease, and wherein utilizing the statistical sampling comprises formulating and obtaining queries based on the data set and processing and responding to the queries, the processing comprising, for each query:

evaluating, by the one or more processors, the query to determine if a prospective response to the query is a single value pulled from a single data set;

based on determining that the prospective response to the query is the single value pulled from the single data set, assigning, by the one or more processors, the query to a given computing resource in the distributed computing environment; and based on determining that the prospective response to the query, distributing, by the one or more processors, the query over a group of computing resources of the distributed computing environment to maximize efficiency, wherein the distributing comprises assigning each computing resource of the group of computing resources a portion of the query to execute in parallel with at least one other computing resource of the group of computing resources executing another portion of the query;

tuning, by the one or more processors, the one or more machine learning algorithms by applying the one or more machine learning algorithms to the training set of data;

dynamically adjusting, by the one or more processors, the common features comprising the one or more patterns to improve accuracy such that the one or more machine learning algorithms can distinguish patient data indicating the orphan disease from patient data that does not indicate the orphan disease; and determining, by the one or more processors, based on applying the one or more machine learning algorithms to data related to the undiagnosed patient, a probability, wherein the probability is a numerical value indicating a percentage of commonality between the data related to the undiagnosed patient and the one or more patterns, wherein the probability indicates a probability that the undiagnosed patient will be diagnosed with the orphan disease in the future.

\* \* \* \* \*